(12) United States Patent
Li et al.

(10) Patent No.: US 10,640,801 B2
(45) Date of Patent: May 5, 2020

(54) DEVICES AND METHODS USING MODIFIED PAPER ELECTRODES FOR THE DETECTION OF HEMOGLOBIN A1C AND GLUCOSE

(71) Applicants: XiuJun Li, El Paso, TX (US); Gilberto Henao-Pabon, El Paso, TX (US)

(72) Inventors: XiuJun Li, El Paso, TX (US); Gilberto Henao-Pabon, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 316 days.

(21) Appl. No.: 15/276,408

(22) Filed: Sep. 26, 2016

(65) Prior Publication Data

US 2017/0088875 A1    Mar. 30, 2017

Related U.S. Application Data

(60) Provisional application No. 62/233,051, filed on Sep. 25, 2015.

(51) Int. Cl.
| | | |
|---|---|---|
| *C12Q 1/00* | (2006.01) | |
| *G01N 33/72* | (2006.01) | |
| *G01N 21/77* | (2006.01) | |
| *C07F 5/02* | (2006.01) | |

(52) U.S. Cl.
CPC .............. *C12Q 1/006* (2013.01); *C12Q 1/003* (2013.01); *G01N 33/723* (2013.01); *C07F 5/025* (2013.01); *G01N 2021/7769* (2013.01)

(58) Field of Classification Search
None
See application file for complete search history.

(56) References Cited

U.S. PATENT DOCUMENTS

| | | | | |
|---|---|---|---|---|
| 2010/0089774 | A1* | 4/2010 | Manohar | G01N 27/3271 205/792 |
| 2012/0261257 | A1* | 10/2012 | Vanjari | G01N 27/3272 204/403.06 |
| 2013/0171369 | A1* | 7/2013 | Wang | C12Q 1/006 427/535 |

OTHER PUBLICATIONS

Dictionary.com, Definition of "anodize". 2 pgs. accessed on Sep. 14, 2018 (Year: 2018).*
Vasu et al. "Non-enzymatic electronic detection of glucose usingaminophenylboronic acid functionalized reduced graphene oxide" Sensors and Actuators B: Chemical B 221 (2015) 1209-1214 (Year: 2015).*
Thiruppathi et al. "A dually functional 4-aminophenylboronic acid dimer for voltammetric detection of hypochlorite, glucose and fructose" Microchim Acta (2017) 184:4073-4080 (Year: 2017).*
Baghayeri, "Glucose sensing by a glassy carbon electrode modified with glucose oxidase and a magnetic polymeric nanocomposite," *RSC Advances*, vol. 5, 2015, pp. 18267-18274.
Bunn et al., *The Journal of Clinical Investigation* 1976, 57:1652-59.
Cai et al., "Direct electron transfer and bioelectrocatalysis of hemoglobin at a carbon nanotube electrode." *Analytical Biochemistry*, vol. 325, No. 2, 2004, pp. 285-292.
Chen et al., "Monitoring the Allosteric Transition and CO Rebinding in Hemoglobin with Time-Resolved FTIR Spectroscopy," *Journal Phys. Chem. A*, vol. 106, No. 14, 2002, pp. 3413-3419.
Chou et al., "Demonstration of the importance of oxygenated species at the ends of carbon nanotubes for their favourable electrochemical properties." *Chemistry Communication*, vol. 7, 2005, pp. 842-844.
Delfino et al., "Enzyme distribution and secondary structure of sol-gel immobilized glucose oxidase by micro-attenuated total reflection FT-IR spectroscopy." *Materials Science and Engineering C*, vol. 33, No. 1, 2013, pp. 304-310.
Dungchai et al., "Electrochemical detection for paper-based microfluidics." *Analytical Chemistry*, vol. 81, No. 14, 2009, pp. 5821-5826.
Genuth et al., "Follow-up report on the diagnosis of diabetes mellitus." *Diabetes Care*, vol. 26, No. 11, 2003, pp. 3160-3167.
Gunasekaran et al., "FTIR Spectral Study on Jaundice Blood Samples Before and After Treatment," *Asian Journal of Chemistry*, vol. 22, No. 1, 2010, pp. 51-56.
Hua et al., "Glucose sensor based on an electrochemical reduced graphene oxide-poly(L-lysine) composite film modified GC electrode." *Analyst*, vol. 137, No. 24, 2012, pp. 5716-5719.
Hui et al., "Direct electrochemistry of glucose oxidase based on Nafion-Graphene-GOD modified gold electrode and application to glucose detection ," *Materials Letters*, vol. 108, 2013, pp. 88-91.
Janegitz et al., "Direct electron transfer of glucose oxidase at glassy carbon electrode modified with functionalized carbon nanotubes within a dihexadecylphosphate film," *Sensors and Actuators B*, vol. 158, No. 1, 2011, pp. 411-417.
Ji et al., "Oxygenated edge plane sites slow the electron transfer of the ferro-/ferricyanide redox couple at graphite electrodes." *Chem PhysChem*, vol. 7, No. 6, 2006, pp. 1337-1344.
Kang et al., "Glucose oxidase-graphene-chitosan modified electrode for direct electrochemistry and glucose sensing." *Biosensors and Bioelectronics*, vol. 25, No. 4, 2009, pp. 901-905.
Kim et al., "Disposable amperometric glycated hemoglobin sensor for the finger prick blood test." *Analytical Chemistry*, vol. 85, No. 13, 2013, pp. 6536-6543.
Kurusu et al., "The advantage of using carbon nanotubes compared with edge plane pyrolytic graphite as an electrode material for oxidase-based biosensors." *Analyst*, vol. 131, No. 12, 2006, pp. 1292-1298.
Lan et al., "Paper-based electroanalytical devices with an integrated, stable reference electrode." *Lab on Chip*, vol. 13, No. 20, 2013, pp. 4103-4108.

(Continued)

*Primary Examiner* — Thane Underdahl
(74) *Attorney, Agent, or Firm* — Norton Rose Fulbright US LLP

(57) ABSTRACT

Certain embodiments are directed to sensors that enable the use of optimized biocompatible materials such as pre-anodized paper printed electrode transducer to detect binding of a target agent, wherein the surface is modified or functionalized through zero length cross-linker so that it interacts with or specifically binds a target such as sugars (glucose) or glycated proteins (HgbA1c).

7 Claims, 19 Drawing Sheets

(56) References Cited

OTHER PUBLICATIONS

Laviron, "General expression of the linear potential sweep voltammogram in the case of diffusionless electrochemical systems," *J. Electroanal. Chem.*, vol. 101, No. 1, 1979, pp. 19-28.
Liang et al., "Direct Electrochemistry of Glucose Oxidase at a Gold Electrode Modified with Single-Wall Carbon Nanotubes," *Sensors*, vol. 3, 2003, pp. 544-554.
Liu et al., "Paper-Based Electrochemical Biosensors: From Test Strips to Paper-Based Microfluidics," *Electroanalysis*, vol. 26, No. 6, 2014, pp. 1214-1223.
Liu et al., "An electrochemical glucose biosensor based on graphene composites: use of dopamine as reducing monomer and as site for covalent immobilization of enzyme," *RSC Advances*, vol. 4, 2014, pp. 43624-43629.
Lopez-Jaramillo et al., *Diabetology & Metabolic Syndrome*, 2014, 6:31.
Malasevic et al., "Synthesis of few-layer graphene via microwave plasma-enhanced chemical vapour deposition." *Nanotechnology*, vol. 19. No. 30, 2008, 305604.
Marcos et al., "Automatic determination of Michaelis-Menten constants by the variable flow-rate technique," *Analytica Chimica Acta*, vol. 283, No. 1, 1993, pp. 429-438.
Martinez et al., "Diagnostics for the developing world: microfluidic paper-based analytical devices." *Analytical Chemistry*, vol. 82, No. 1, 2010, pp. 3-10.
Nie et al., *Lab on a chip*, 2010, 10:3163-69.
Nie et al., *Lab on a Chip*, 2010, 10:477-83.
Prasad et al., "The role of oxygen functionalities and edge plane sites on screen-printed carbon electrodes for simultaneous determination of dopamine, uric acid and ascorbic acid," *Electrochemistry Communications*, vol. 10, No. 4, 2008, pp. 559-563.
Prasad et al., "Enhanced electroactivity and substrate affinity of microperoxidase-11 attached to pyrene-linkers π-π stacked on carbon nanostructure electrodes," *RSC Advances*, vol. 5, 2015, pp. 11845-11849.
Prasad et al., "Mediatorless catalytic oxidation of NADH at a disposable electrochemical sensor," *Sensors and Actuators B*, vol. 123, No. 2, 2007, pp. 715-719.
Razmi et al., "Graphene quantum dots as a new substrate for immobilization and direct electrochemistry of glucose oxidase: application to sensitive glucose determination." *Biosensors and Bioelectronics*, vol. 41, 2013, pp. 498-504.
Sehat et al., "Fast Immobilization of Glucose Oxidase on Graphene Oxide for Highly Sensitive Glucose Biosensor Fabrication," *Int. J. Electrochem. Sci.*, vol. 10, No. 1, 2015, pp. 272-286.
Shirale et al., "Studies of immobilized glucose oxidase on galvanostatically synthesized poly(N-methylpyrrole) film with PVS-NaNO$_3$ composite dopant," *Int. J. Electrochemistry Sci.*, vol. 1, No. 2, 2006, pp. 62-70.
Wang et al., "Direct electrochemistry of cytochrome c at a glassy carbon electrode modified with single-wall carbon nanotubes." *Analytical Chemistry*, vol. 74, 2002, pp. 1993-1997.
Wu et al., "Direct electrochemistry of glucose oxidase in a colloid Au-dihexadecylphosphate composite film and its application to develop a glucose biosensor." *Bioelectrochemistry*, vol. 70, No. 2, 2007, pp. 335-341.
Yang et al., "An electrochemically preanodized screen-printed carbon electrode for achieving direct electron transfer to glucose oxidase," *Electrochemistry Communications*, vol. 10, No. 7, 2008, pp. 1094-1097.
Zhang et al., "A novel glucose biosensor based on direct electrochemistry of glucose oxidase incorporated in biomediated gold nanoparticles-carbon nanotubes composite film," *Sensors and Actuators B: Chemical*, vol. 158, No. 1, 2011, pp. 23-27.
Zhao et al., "Direct electron transfer and conformational change of glucose oxidase on carbon nanotube-based electrodes," *Carbon*, vol. 48, No. 5, 2010, pp. 1508-1514.
Zhou et al., "Fabrication of electrochemical interface based on boronic acid-modified pyrroloquinoline quinine/reduced graphene oxide composites for voltammetric determination of glycated hemoglobin." *Biosensors and Bioelectronics*, vol. 64, 2015, pp. 442-448.

\* cited by examiner

Log Scan Rate V/s versus log Peak Current μA (A)
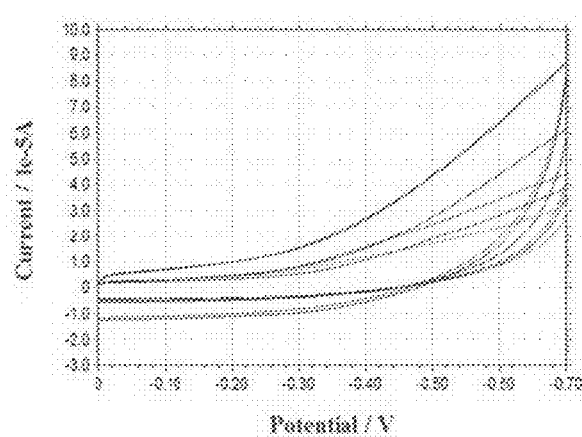
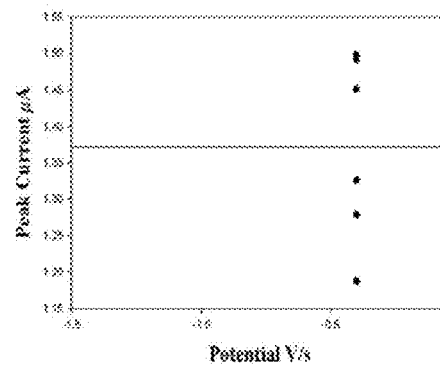
(B)
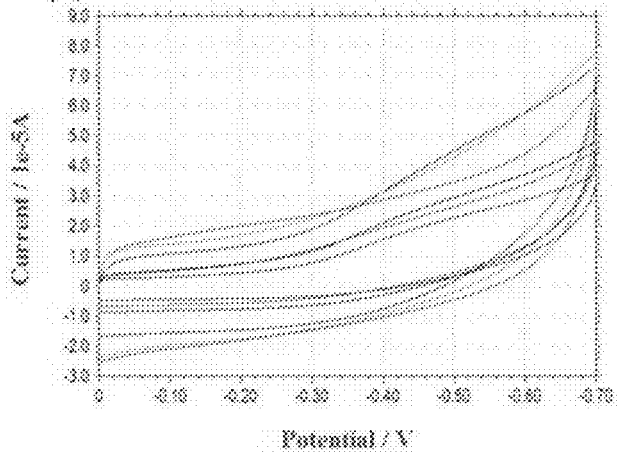
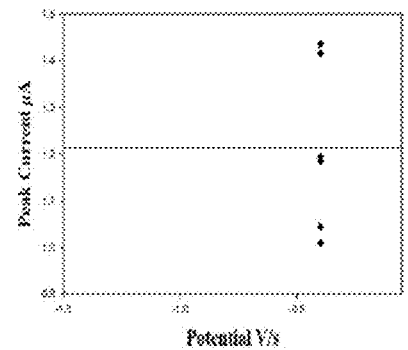
FIGS. 6A-6B

DEVICES AND METHODS USING MODIFIED PAPER ELECTRODES FOR THE DETECTION OF HEMOGLOBIN A1C AND GLUCOSE

This application claims priority to U.S. Provisional Application No. 62/233,051 filed Sep. 25, 2015, which is incorporated herein by reference in its entirety.

BACKGROUND

Diabetes Mellitus (DM) is a fast growing epidemic disease (Centers for Disease Control and Prevention, *National Diabetes Fact Sheet*, 2011). 29.1 million children and adults in the U.S. have DM, (9.3% of the population)(American Diabetes Association, *Fast facts: data and statistics about diabetes*, Revision March 2013; Centers for Disease Control and Prevention. *Diabetes report card 2012: National state profile of Diabetes and its Complications*, August 2012) with 21 million people being diagnosed with DM and 8.1 million people being undiagnosed (Centers for Disease Control and Prevention, *Diabetes report card 2012: National state profile of Diabetes and its Complications*, August 2012; Centers for Disease Control and Prevention, Department of Health and Human Services, *National Diabetes Statistics Report. 2014 National Diabetes data fact sheet*). Eighty-six million people are classified as pre-diabetic. DM is defined by fasting hyperglycemia >200 mg/dL Hyperglycemia occurs when the body produces low levels of insulin or the insulin produced is deficient. DM can be classified as: (1) Type 1 Diabetes Mellitus (T1DM) where the body produced no insulin by failure at the beta cells of the islets of Langerhans in the pancreas, which can affect adults and children (Genuth et al., *Diabetes Care* 2003, 26:3160-67; WHO/IDF. Definition and Diagnosis of DM and Intermediate Hyperglycemia. *WHO* 2006, 21) (2) Type 2 Diabetes Mellitus (T2DM) caused by an insufficient production of insulin by the pancreas, beta cells, and an insulin resistance by the cells specifically in the liver, the muscles and the fat tissue, either existing in the presence of normal insulin levels (Genuth et al., *Diabetes Care* 2003, 26:3160-67; WHO/IDF. Definition and Diagnosis of DM and Intermediate Hyperglycemia. WHO 2006, 21; Vijan, *Annals of Internal Medicine,* 2010, 2:150(5)) and (3) Diabetes Gestational (GDM), which is a condition exhibited in pregnant women wherein they develop high blood glucose levels during pregnancy, especially during the third trimester (Moore et al., *Medscape*, Jul. 7, 2014). The screening for DM and Pre-Diabetes are the primary goals for diabetes care (U.S. Preventive Services Task Force. *Screening for type 2 diabetes mellitus in adults. Recommendation statement*, Published June 2008).

Hypertension and dyslipidemia are clear risk factor for Cardio Vascular Disease (CVD) and DM (Lopez-Jaramillo et al., *Diabetology & Metabolic Syndrome*, 2014, 6:31). CVD is the major causes of morbidity and mortality for individuals with DM. Glucose is a key parameter for control of DM. DM can be diagnosed with two basic lab tests: (1) Fasting plasma glucose level at or above 7.0 mMol/L (126 mg/dL) and (2) Glycate haemoglobin (HgbA1c) at or above 6.5. Pre-diabetes is defined as a condition in which individuals have blood glucose and HgbA1c levels higher than normal, but not high enough to be classified as diabetes. The formation of HbA1c is mainly dependent on the interaction between blood glucose concentration and the life span of red blood cells (RBC). Glycated hemoglobin can be directly proportional to a time-averaged concentration of glucose within the red blood cell, and the fact that HbA1c accumulates through the red cell's life-span, which explains why young red cells have lower amounts of HbA1c than old red cells (Bunn et al., *The Journal of Clinical Investigation* 1976, 57:1652-59). HgbA1c reflects the average of blood glucose level for last 2-3 months, the daily fluctuations of the glucose level cannot affect the HgbA1c levels, and is a more accurate index for diagnosis and long-term monitoring and control for the DM.

There remains a need for additional devices, sensors, and methods for detecting glycated hemoglobin.

SUMMARY

Self-monitoring of blood glucose (SHBG) has been established as a valuable tool for the management of diabetes, the goal of SHBG is to help the patient to achieve and maintain normal blood glucose concentration, in order to delay or prevent the progression of micro-vascular (retinopathy, nephropathy, neuropathy), and macro-vascular (stroke, coronary artery disease), complications. Glycated Hemoglobin (HgbA1c), may be considered a biomarker for the presence and severity of hyperglycemia, implying diabetes mellitus (≥6.5%) or Pre-diabetes state (≥5.7%-<6.5%), and also can be considered as risk factor. HgbA1c assesses the effectiveness of the therapy by monitoring long-term serum glucose regulation, the implementation of HgbA1c control methods soon after the diagnosis of diabetes is also associated with long-term reduction in micro-vascular disease. HgbA1c is not recommended as frequently as glucose, but, its HgbA1c role in diagnosis, prevention and management is critical. HgbA1c has a significant correlation over the estimated average glucose (eAG) or mean blood glucose (MBG).

Certain embodiments are directed to sensors that enable the use of optimized biocompatible materials such as: (i) pre-anodized paper printed electrode transducer to detect HgbA1c; (ii) Surface pretreatment used as a method of modification by employing electrochemical pretreatment of electrodes, requires treating the carbon electrode at high potential in a given solvent or electrolyte generating surface functional groups, carboxyl, carboxylic, phenol, hydroxyl, epoxy, which function as mediators or hotspots for the covalent binding of biological molecules to speed up electron transfer rate to enhance the sensitivity and reproducibility of the electrode; (iii) 3-AminoPhenyl-Boronic acid (APBA) with the ability to interact with sugars, bind glucose, and can capture glycated proteins, HgbA1c; (iv) HgbA1c with its catalytic activity towards the reduction of $H_2O_2$ could be used as a measure to monitor the HgbA1c concentration. As used herein, anodizing refers to an electrolytic passivation process used to increase the thickness of an oxide layer.

Certain embodiments are directed to a glycated hemoglobin sensor comprising an anodized conductive ink on a support having a functionalized surface coupled to a sugar reactive moiety. In certain aspects the support is a paper support. The sugar reactive moiety can be 3-amino-phenylboronic acid (APBA). In certain aspect a sensor can be incorporated into a diagnostic device or detection system for glycated hemoglobin.

Carbon-based inks can be used as conductors on for example printed circuits and electrodes for sensors. A carbon-based ink is an ink containing a carbon particulate such as graphite, amorphous carbon, or a fullerene, suspended in a binder and a solvent. These inks are applied on a surface via a number of deposition techniques, including painting on with a brush, syringe application, and screen printing. The ink is allowed to dry and the resulting carbon-coated surface is subjected to a treatment at temperatures ranging from 50° C. to several hundred degrees Celsius. This high temperature treatment, or curing, is necessary to attain high conductivity in the resulting composite conductors. In certain aspects the conductive ink is anodized or pre-anodized.

Other embodiments are directed to a glycated hemoglobin sensor comprising an anodized support coupled to a glycated hemoglobin binding moiety. In certain aspects the support is a paper support. The glycated hemoglobin binding moiety can be 3-amino-phenyl-boronic acid (APBA). In certain aspect a sensor can be incorporated into a diagnostic device or detection system for glycated hemoglobin.

Certain embodiments are directed to methods of detecting glycated hemoglobin comprising (i) contacting a sensor described herein with a sample to form an exposed sensor, and (ii) contacting the exposed sensor with a glycated hemoglobin detection reagent that produces a detectable signal in the presence of hemoglobin. In certain aspects the detection reagent is $H_2O_2$. In a further aspect the detectable signal is an electric signal or the production of electrons.

In certain embodiments the sensor support is partially paper or is an all paper device. Paper is a thin material produced by pressing together moist fibers, typically cellulose pulp derived from wood or grasses and drying them into flexible sheets. The thickness of paper is often measured by caliper, which is typically given in thousandths of an inch. Paper can be characterized by weight. In the United States, the weight assigned to a paper is the weight of a ream (500 sheets) before the paper is cut to size. For example, a ream of 20 lb, 8.5 in×11 in (216 mm×279 mm) paper weighs 5 pounds, because it has been cut from a larger sheet into four pieces. The density of paper ranges from 250 kg/m$^3$ (16 lb/cu ft) for tissue paper to 1,500 kg/m$^3$ (94 lb/cu ft) for some specialty paper. In certain aspect the paper is a porous blotting paper having a thickness of 0.5 to 2 mm, including all values there between. In a further aspect the paper is chromatography paper having a thickness 0.05 to 0.25 mm and pores having a diameter of 5 to 15 µm. The paper can be modified to provide electric conductivity or electrical pathways, as well as functionalized to allow coupling with other moieties. A paper device can be designed to have electrically conductive regions that form channels and chambers that allow the flow of electrons. For example, the paper can be anodized. Paper can be cut into appropriate shapes and/or layered so as to produce an all paper sensor or device.

The phrase "specifically binds" to a target refers to a binding reaction that is determinative of the presence of the target in the presence of a heterogeneous population of other biologics. Thus, under designated conditions, a specified molecule binds preferentially to a particular target and does not bind in a significant amount to other biologics present in the sample.

As used herein, the term "sample" or "test sample" generally refers to a material suspected of containing one or more targets. The test sample may be used directly as obtained from the source or following a pretreatment to modify the character of the sample. The test sample may be derived from any biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. In certain aspects the sample is blood or serum or a fraction thereof. The test sample may be pretreated prior to use, such as preparing plasma from blood, diluting viscous fluids, lysing or disrupting microbes in the sample, and the like. Methods of treatment may involve shearing, filtration, precipitation, dilution, distillation, mixing, concentration, inactivation of interfering components, and/or the addition of reagents.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 5A). CV response of PA-PPE immobilized with APBA-HgbA1c 3.125% in 0.1 M PBS at a scan rate of 50-300 mV/s, and (FIG. 5B), plots of anodic and cathodic peak current with scan rate, (FIG. 5C) show the plot of the log of Scan Rate (V/s) and log of Peak current (μA), with linear relationship and slope of −0.4511.

FIGS. 6A-6B. Cyclic Voltammetry (CV) for different electrodes PA-PPE-APBA-HgbA1c with the same HgbA1c concentration. FIG. 6A shows PA-PPE-APBA-HgbA1c-3.125% and FIG. BB shows PA-PPE-APBA-HgbA1c-0.195%, the peaks current, probe with 0.1 M PBS and $H_2O_2$ 5 mM and the plot between the peak current and the potential applied, with the corresponding slope for each graphic.

(FIG. 7A) show HgbA1c at higher concentrations (6.25% to 0.195%) and (FIG. 7B) show HgbA1c at lower concentrations (0.00488% to 0.00030%) with characteristic response inside the linear relationship show through plot: Y=log the peak current μA and X=log the HgbA1c % concentration (FIG. 7C). Log HgbA1c concentration versus Log peak current for PA-PPE-APBA-HgbA1c (FIG. 7D).

(FIG. 13A). CV response of PA-PPE immobilized with GOX in 0.1 M PBS at a scan rate of 50-200 mV/s, and (FIG. 13B), plots of anodic ($i_{pa}$) and cathodic ($i_{pc}$) peak current versus scan rate.

DESCRIPTION

Figure 1:
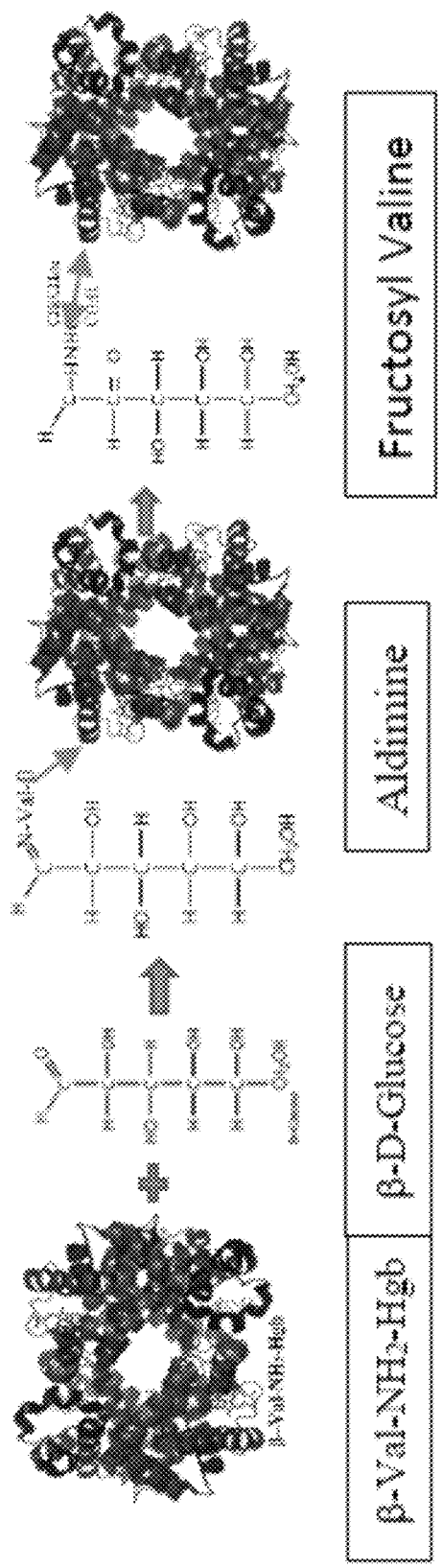
FIG. 1. Shows the condensation of HgA0-($\alpha_2$-$\beta_2$)-($\beta$-Val-NH$_2$) with $\beta$-D-Glucose.

HgbA1c is formed by condensation of glucose molecule with the N-terminal amino group of valine of the β-chains of HgbA$_0$ ($\alpha_2\beta_2$) undergoing an Amadori rearrangement to form a more stable ketoamine linkage, a post-translational modification of HgbA$_0$ (FIG. 1). The extremely slow conversion of HgbA$_0$ to HgbA1c suggests a non-enzymatic process. As a consequence turnover of red blood cells and the concentration of glucose: 50% of HgbA1c value is the result of the glucose exposure during the previous 30 days period, 40% of HgbA1c value is the result of the glucose exposure during the 30-90 days period and 10% value formed by glucose exposure during the previous 91-120 days period (Henrichs and Helmut, *HbA1c-glycated hemoglobin and diabetes mellitus*, 1$^{st}$. ed. Bremen UNI-MED 2009). HgbA1c levels clinical reference are 5% to 20% with normal values 4% to ≤5.5%. A 1% change in the HgbA1c level reflects a fluctuation of Mean Blood Glucose (MBG) concentration by approximately 2 mM [MBG (mmol/L)= (1.98×HbA1c)−4.29], ~35.64 mg/dL.

Figure 2:
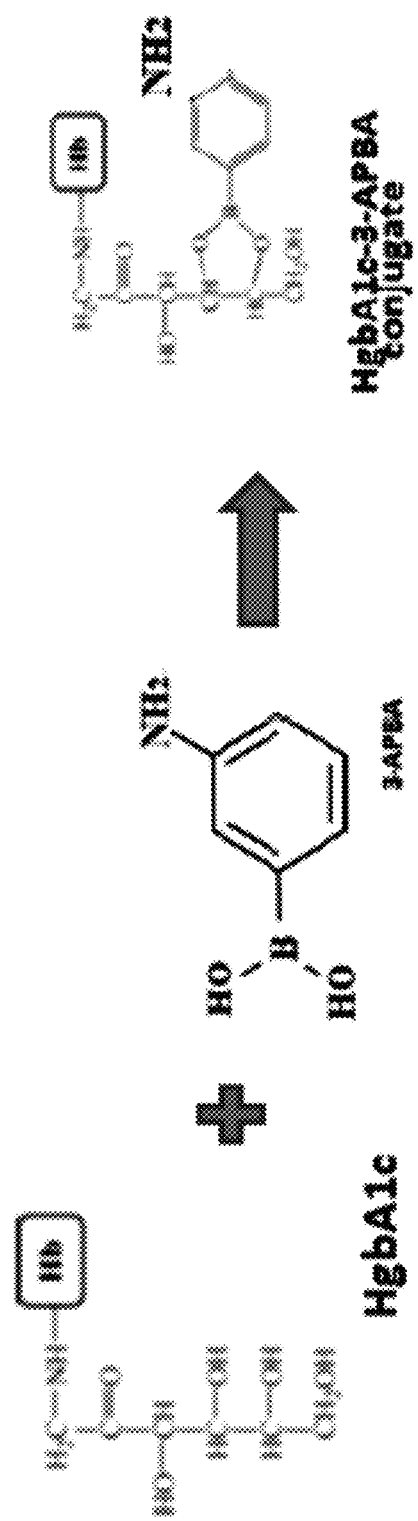
FIG. 2. Shows the conjugation of HgbA1c and 3-Amino-Phenyl-Boronic Acid (3-APBA).

HgbA1c measures electrochemically (Amperometric methods) are based in the recognition of amino-phenylboronic acid (APBA) which interact with the sugars, and have the ability to bind glucose and glycated proteins through boronic acid-diol bound. Boronic acid can covalently bind to 1,2 or 1,3-diol group and the cis-diol group of the surface sugar from glycated proteins under weak alkaline conditions, to form reversible cyclic boronic esters (FIG. 2). The catalytic reduction of $H_2O_2$ by HgbA1c can be monitored as an analytical signal in a sensor HgbA1c electrode, due to Hgb have four iron heme groups that catalyze the reduction reaction of $H_2O_2$ (Kim et al., *Analytical Chemistry*, 2013, 85:6536-43; Sheikloleslam et al., Electrochemical biosensor for glycated hemoglobin (HbA1c), Chapter 13 in *Biosensor for Health Environment and biosecurity*, Prof. Pier Andrea Serra Ed. July 2011). Reduction of hydrogen peroxide at a platinum electrode recognizes the number of electrons transfers, and this electron flow is proportional to numbers of HgbA1c molecules present in blood, this reduction of $H_2O_2$ is specifically catalyzed by HgbA1c. This amperometric assay of HgbA1c is direct electron transfer detection without enzymes for the intact glycated protein recognition. APBA serves 2 functions: (i) selective binding to HbA1c over the other immobilized hemoglobins (using boronic acid part) and (ii) Participation in the electrochemical reaction for HbA1c measurement through its ferrocene part. The new generation of HgbA1c biosensor are reagentless, an amperometric HgbA1c biosensor, based on direct electron transfer (DET) between the cofactor APBA and HgbA1c and the electrode surface without mediators.

Microfluidics and micro-electro-mechanical-systems (MEMS) technology have enabled the miniaturization of biomedical and chemical analysis systems. Micro-scale biosystems can provide even superior performance compared with their large-scale counterparts.

Direct electron transfer (DET) of electrons can be applied in biological studies on mechanisms and metabolic process involving also redox transformations of enzymes, and the use of nanostructures to facilitate effectively the DET shorten the electron tunneling distance at the immobilized enzyme on the surface of the nanotube electrode. The redox potential happening in the anode must be as negative as possible to give a maximum potential difference between the anode and the cathode. DET of HgbA1c immobilized on the surface of the electrode can undergo DET, the bio-electro-catalysis is required to build a mediation (APBA) and immobilized glycated protein (HgbA1c) for continuous and efficient electron transfer from the glycated protein to the electrode surface. The anodic and cathodic peak potentials should be pH dependent, around pH 7.4, like physiologic conditions, the redox potential for the APBA-Hgb is sufficiently negative for anode operation. One reason for DET is the presence of carboxylic group with FTIR at 1715 cm$^{-1}$ and carboxylate groups with FTIR at 1574 cm$^{-1}$, (—C=O, —COOH, —OH). The use or application of redox mediators versus the stimulation (pre-anodization procedure) to increase surface carboxylic and carbonyls group's functionalities on the edge planes shifts the redox potential of the APBA-HgbA1c anode to a more positive potential range than the redox potential of APBA systems.

Oxidation of hydrogen peroxide at a platinum electrode is prone to interference from ascorbic acid and uric acid. The use of a matrix appropriate to immobilize GOX is a more convenient way to achieve the purpose of DET and even with greater sensitivity and better stability to act as biosensors for glucose. It was reported that (CNT) carbon nanotubes can promote DET due to the presence of oxygen groups on the surface. Ji, Kurusu, and Chou studied the effect of oxygenated in CNT species and the rate of electron transfer was found to be dominated by the features at the end of the CNT, especially the carboxylate groups. The Compton group studied the location and nature of electron transfer processes on CNT modified electrode and concluded that flat edge defects—as in CNT as the key for the catalytic activity of high electro to various biological molecules (Ji et al., *Chem PhysChem* 2006, 7:1337-44; Chou et al., *Chemistry Communication* 2005, 7:842-44; Kurusu et al., *Analyst* 2006, 131:1292-98). Electrochemical biosensors based on enzymes are highly selective, sensitive and faster, and can be used to detect any kind of biological species.

Prasad and Jyh-Myng Zen have reported unique applications of disposable electrodes previously anodized screen-printed carbon (designated as SPCE*) with higher electrochemical activity. The disposable SPCE* with the introduction of the flat edge carbonyl groups was found to act more or less as an electrode graphite edge flat or CNT. Based on the flexibility and robustness of the SPCE*, establishing a simple and easy alternative to allow DET GOX reaction and the discussion on the denaturation of the enzyme (Prasad et al., *Sensors and Actuators B* 2007, 123:715-19; Prasad et al., *Electrochemistry Communications* 2008, 10:559-63).

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Pre-Anodized Paper Electrode (PA-PPE)-3-Aminophenyl-Boronic Acid (APBA)-HbgA1c Matrix Platform A. Materials and Methods (1-ethyl-3[3dimethylaminopropyl] carbodiimide hydrochloride (EDC) and N-Hydroxy succimide (NHS), 3-Aminophenylboronic acid (APBA), were purchased from Sigma Aldrich Co. A Human blood hemolysate as lyophilized glycated hemoglobin (HgbA1c) reference, RM 405 (lyophilized form to about 0.5 ml of a solution of hemolysate of human erythrocytes with a substance concentration of total hemoglobin of 0.23 mmol/L (15 g/L.), were purchased from Sigma Co. A volume of 1 mL of deionized water was added to the lyophilized HgBA1c to reconstitute, allow standing for 15 minutes at room temperature, mix gently and them stored at 4° C. the reconstituted RM 405 was diluted with hemolyzing reagent [(26 mM $NaH_2PO_4$/10 mL,+7.4 mM $Na_2HPO_4$/10 mL) 0.5 mL+0.5 ml of 13.5 mM KCN], the final concentration of HgbA1c was obtained to be a 6.25% in a 0.23 mM hemoglobin. A pH 7.4 phosphate buffer solution (PBS) was used in all studies. Water was obtained from a Millipore purification system. Voltammetric measurements were carried out with a CH Instruments (CHI 627) electrochemical workstation in a three-electrode cell assembly. The two sensing electrodes (PPE, paper electrode and PA-PPE (preanodized)) were fabricated by pattering electrode designs onto a low tack paper, which is subsequently pasted onto a SU8 treated chromatography paper (Dungchai et al., *Analytical Chemistry*, 2009. 81:5821-26), which was then stencil printed by using conductive carbon and Ag/AgCl ink to develop a carbon based working electrode (WE), Counter Electrode (CE) and silver pseudo reference electrode, Ag/AgCl (RE) (Martinez et al., *Analytical Chemistry*, 2010, 82(1):3-10; Lan et al., *Lab on Chip*, 2013, 13:4103-08; Nie et al., *Lab on a Chip*, 2010, 10:3163-69; Liu et al., *Electroanalysis*, 2014, 26:1214-23). The FT-IR spectrum was recorded from Spectrum™ 100 FT-IR Spectrometer from Perkin Elmer™.

Figure 3:
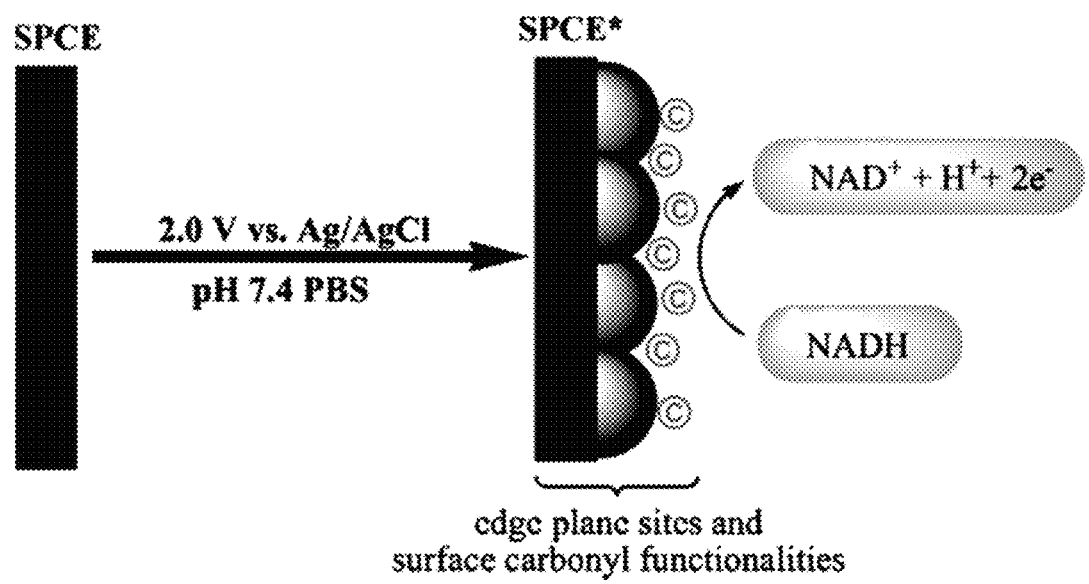
FIG. 3. Shows the sketches for the electrochemical oxidation of NADH at the SPCE* with surface carbonyl functionalities on edge plane sites.
Figure 4A:
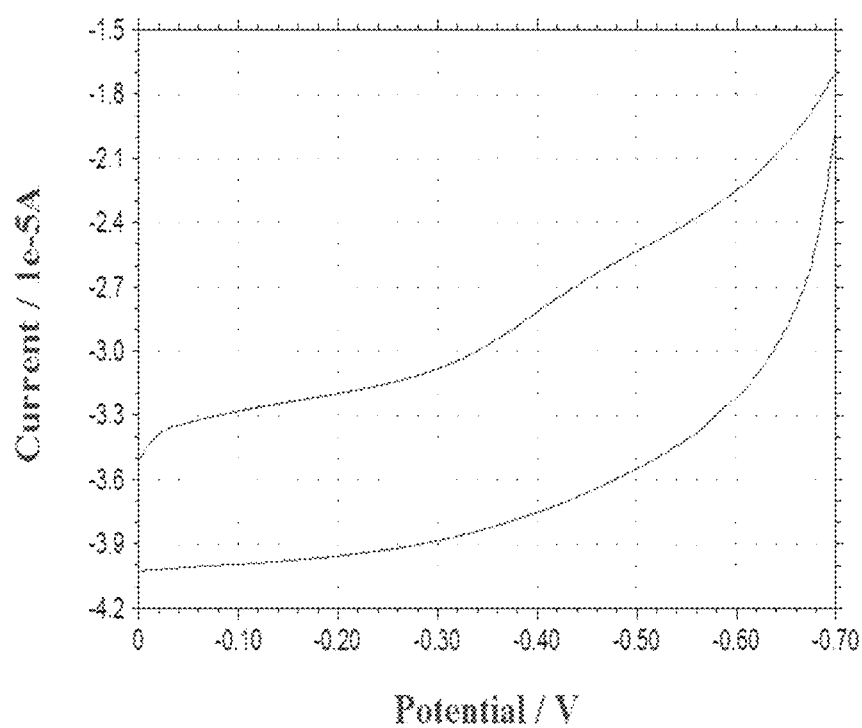
FIGS. 4A-4D. CV response of PA-PPE-HgbA$_1$c immobilized by APBA in 5 mM H$_2$O$_2$ (FIG. 4A) at a scan rate of 50 mV/s; part (FIG. 4B) shows the catalytic reduction peak of 5 mM of H$_2$O$_2$ by the captured HgbA$_1$c compared with PA-PPE-APBA-HgbA$_1$c probe with 0.1 M PBS and part (FIG. 4C) low concentrations of HgbA1c 0.00015% (0 mM, red line; 0.625 mM, blue light line; 1.25 mM, brown line; 2.5 mM green line and 5 mM) and (FIG. 4D) high concentration of HgbA1c 3.125% (0 mM; 1.25 mM; 2.5 mM; 5 mM) show the catalytic reduction peak of $H_2O_2$ in different concentrations.
Figure 4B:
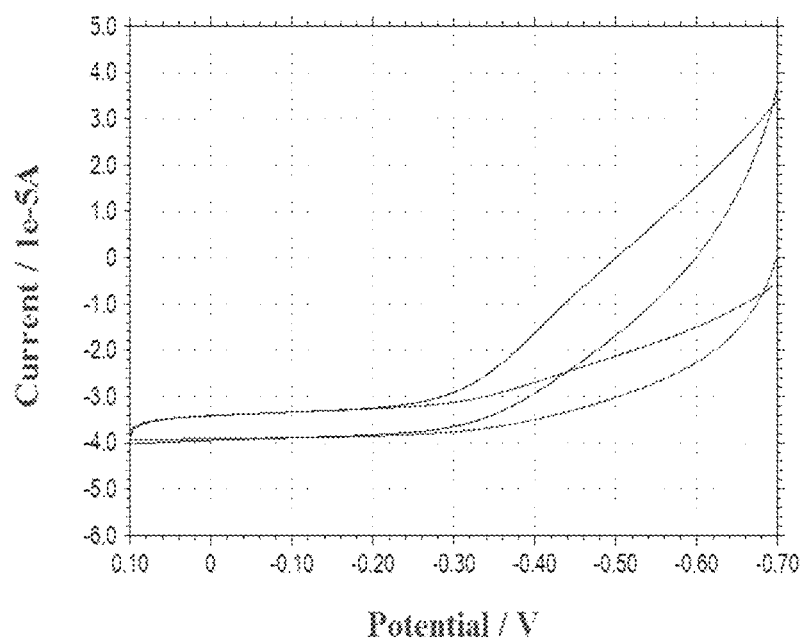
Figure 4C:
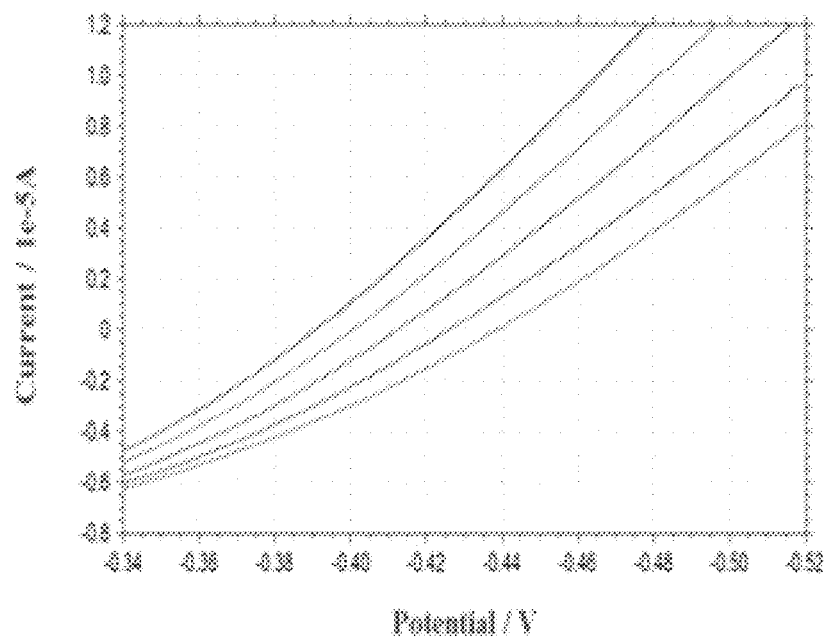
Figure 4D:
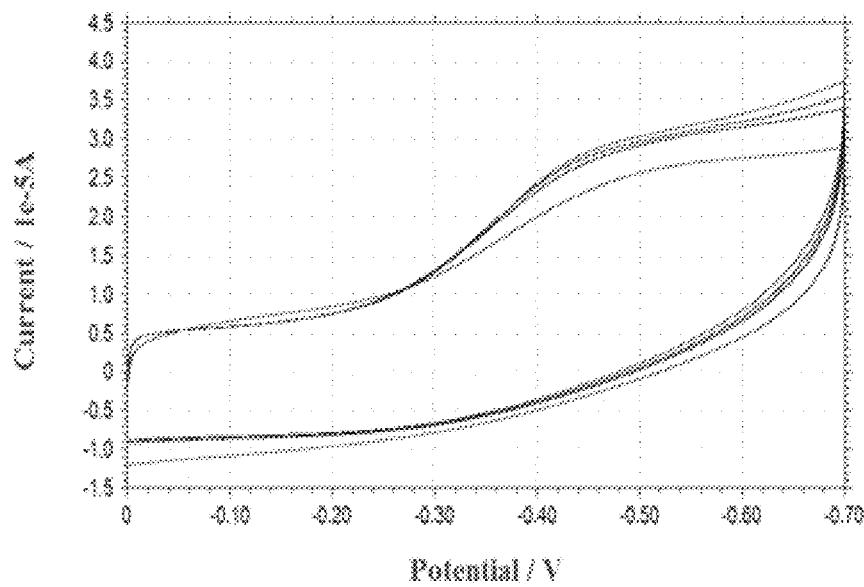

Electrodes are then pre-anodized by applying a potential at 2.0 V vs. Ag/AgCl for 300 s in pH 7.4 PBS to create carbon and oxygen functionalities (FIG. 3), further the immobilization of APBA is carried out through a covalent immobilization (availing EDC/NHS chemistry) fashion by activating the carboxyl functionalities resulted from the pre-anodization technique. The APBA solution is prepared by dissolving 10 mM APBA in 10 mL PBS, and drop coated (5 μL) on to EDC/NHS activated PA-PPE. The electrodes are then dried at room temperature for 1 h and subsequently washed with PBS to remove unbounded APBA. The HgbA1c solution (Lyophilized HgbA1c reconstituted and Haemolyzinf reagent) was added to working electrode and left dry for 30 minutes and them washed with 1 μL of PBS to removed unbounded HgbA1c and evaluated for the electrochemical experiments. The PA-PPE-APBA and PA-PPE-APBA-HgbA1c was evaluated for the electrochemical oxidation with 5 mM of Ruthenium Hexa-amine Chloride $Ru(NH_3)_6Cl_2$ and 5 mM of Potassium Ferrocyanide $K_3Fe(CN)_6$ through direct electron transfer.

A pair of well-defined and nearly symmetric redox peaks can only be observed with a formal potential of −0.34 V to −0.65 V at the PA-PPE-APBA-HgbA1c, which result for redox process of the heme groups of $HgbA_{1c}$ captured on APBA (FIG. 4)(Kim et al., *Analytical Chemistry*, 2013, 85:6536-43); the $HgbA_1c$ was immobilized by PA-PPE-APBA through cis-diol interactions between the diol group of glucose of HgbA1c and the boronic acid group. Overall, the oxygen functionalities and edge plane-like sites formed at the PA-PPE play an important role in facilitating the electron transfer between the APBA-HgbA1c and electrode. The catalytic reduction peak of $H_2O_2$ by the immobilized HgbA1c, appeared around 0.34 V on the PA-PPE-APBA-HgbA1c (lower concentration of HgbA1c, 0.00015% and high concentration of HgbA1c, 3.152%), probe with 0.1 M PBS and different concentrations of $H_2O_2$ (0.625 mM through 5 mM), means that the catalytic process occurs and the reduction current of $H_2O_2$ increases when the concentration of $H_2O_2$ increases.

Figure 5A:
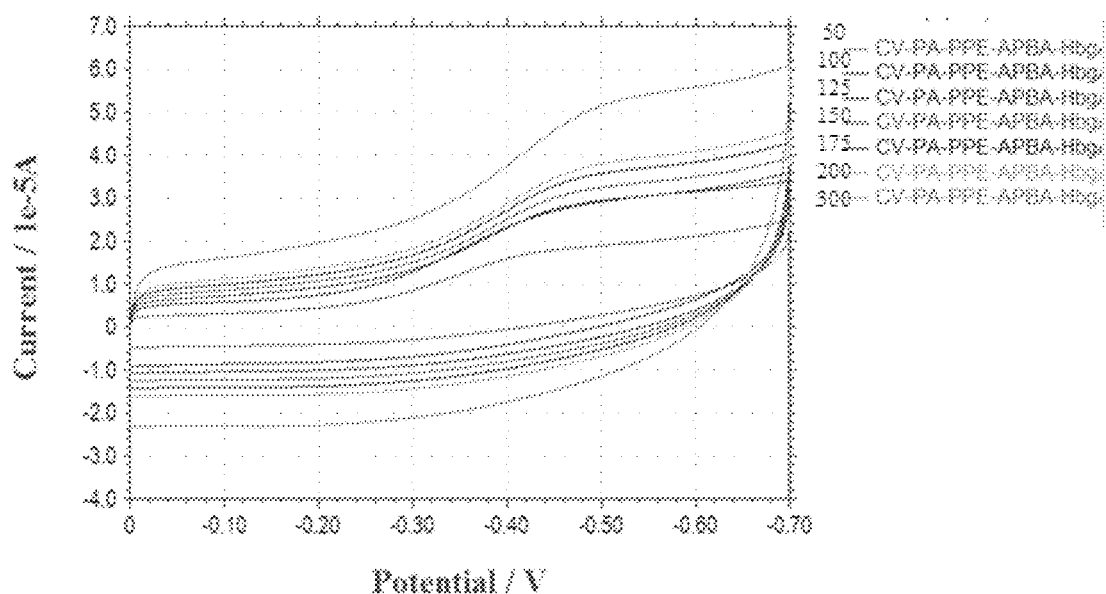
FIGS. 5A-5C.
Figure 5B:
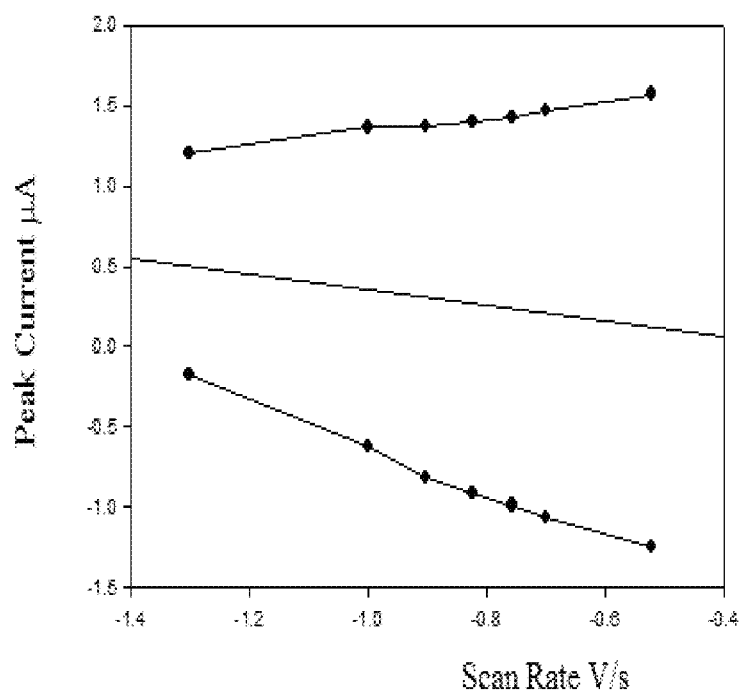
Figure 5C:
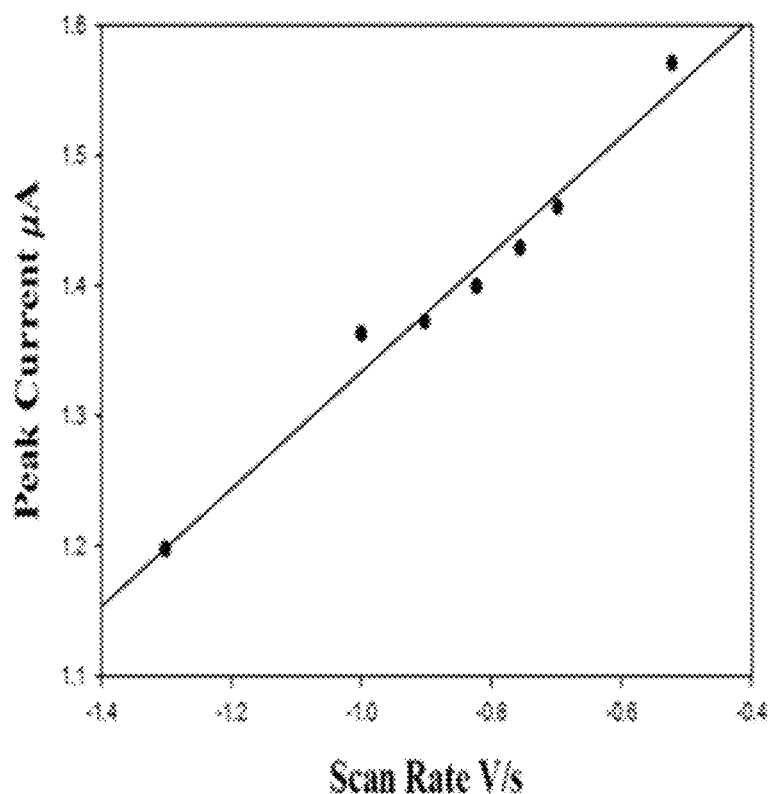

FIG. 5 shows the cyclic voltammograms at different scan rates ranged from 50 to 300 mV/s, and a good linear relationship for the peak current and scan rate (m=0.4511)

indicates a surface-diffusion controlled electrode process. It is thus expected that the APBA-HgbA1c molecule does not extend gradually to an unfolded structure, and its behavior is very similar to voltammetric sensor based on phenylboronic acid-modified pyrroloquinolone (APBA-PPQ) and reduced graphene oxide (Zhou et al., *Biosensors and Bioelectronics*, 2015, 64:442-48).

In order to establish the increased stability and feasibility of the as developed electrode, PA-PPE-APBA-HgbA1c was probed with 0.1 M PBS and $H_2O_2$ 5 mM, to compare the current response developed on HgbA1c immobilized on APBA, with different concentrations of HgbA1c (3.125% and 0.195%) and different electrodes, shown in FIG. 6. The slopes found are between 0.439 and 0.609 that means a diffusion controlled process. For HgbA1c (3.125%) electrode the Median was 1.3884, the SD was 0.1275, the SE 0.0521, the 95% conf. 0.1338 and 99% conf. 0.2099 and for HgbA1c (0.195%) electrode the median was 1.1886, the SD was 0.1793, the SE was 0.0732, the 95% conf. was 0.1182 and the 99% conf. was 0.2952.

Figure 7A:
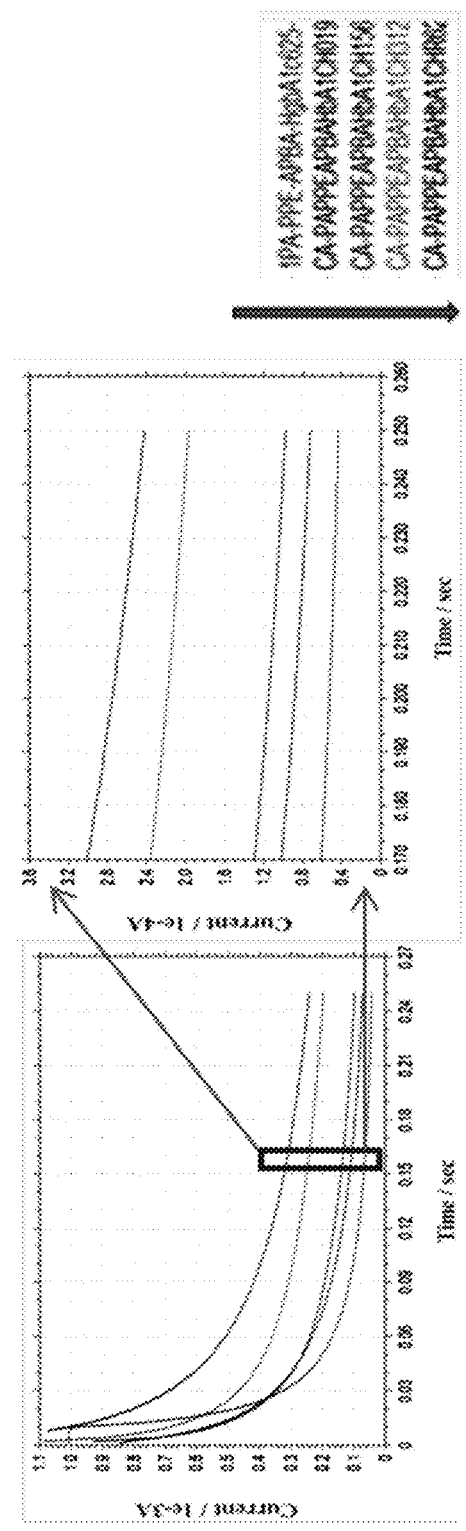
FIGS. 7A-7D. Chronoamperometric (CA) response for PA-PPE-APBA-HgbA1c towards different concentrations of HgbA1c, probe with 0.1 M PBS, (pH 7.4) and $H_2O_2$ 5 mM.
Figure 7B:
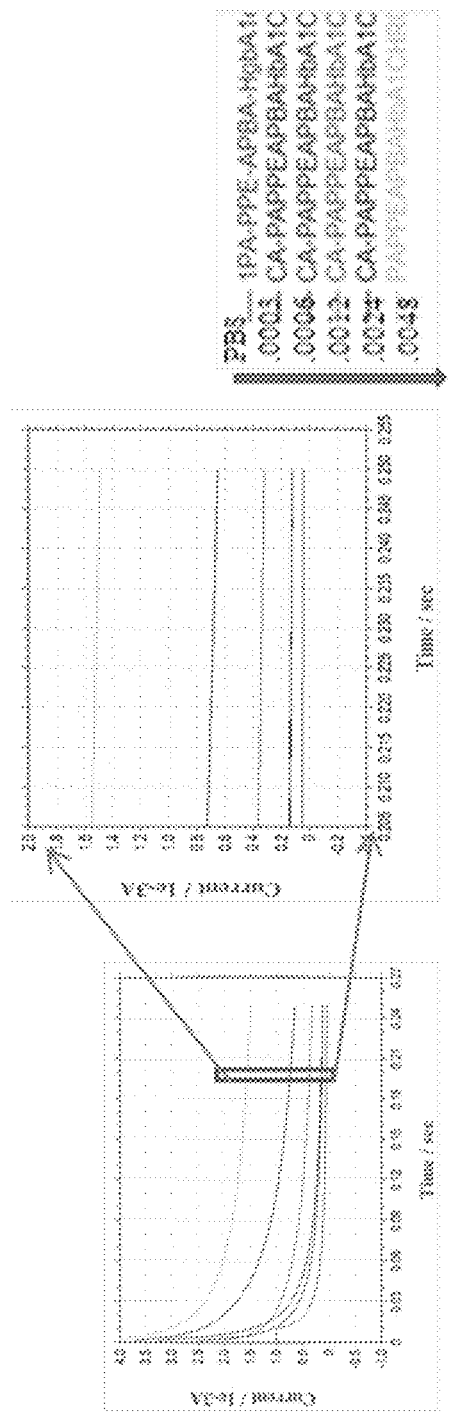
Figure 7C:
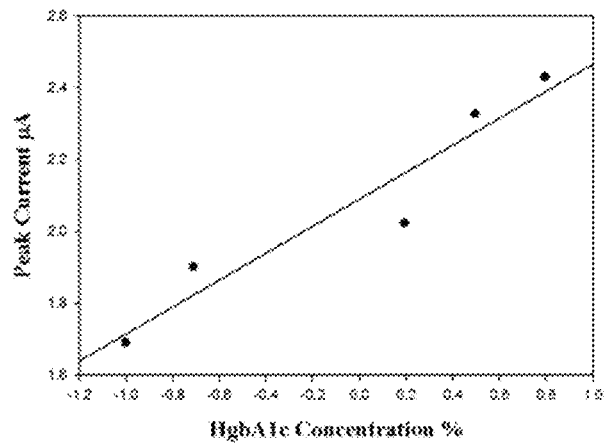
Figure 7D:
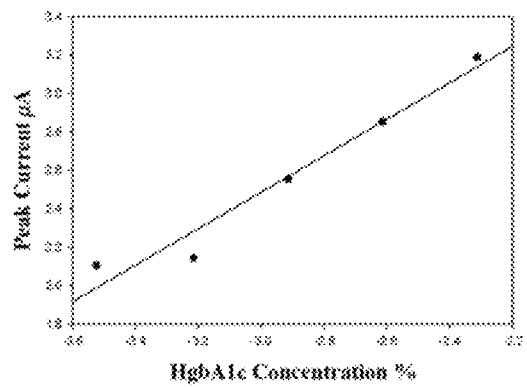

The amperograms for the reduction of HgbA1c were recorded using the sensor probe in 0.1 M PBS (pH 7.4) and $H_2O_2$ 5 mM containing different concentration of HgbA1c. FIG. 7 shows the chronoamperometric (CA) responses of HgbA1c reduction at different concentrations of HgbA1c at −0.55 V. As the increasing HgbA1c captured, the current catalyst of HgbA1c concentration increases, due to the reduction of the HgbA1c is specifically catalyzed by $H_2O_2$ (Kim et al., *Analytical Chemistry*, 2013, 85:6536-43). FIG. 7A and FIG. 7B show the CA responses at higher (0.195 through 6.25%) and lower HgbA1c concentrations ($30\times10^{-5}$ through $488\times10^{-5}$%) respectively, and FIG. 7C shows the plot for each correspondent HgbA1c concentrations. The analysis of each plot in FIG. 7C shows: for higher concentrations of HgbA1c (SD: 0.1958, SE: 0.0122, the 95% Conf. 0.0241, the 99% Conf. 0.0317, and $R^2$ 0.9173) and for lower concentration of HgbA1c: (SD=0.4632, SE 0.2071, the 95% Conf. 0.5751, the 99% Conf. 0.9535 and $R^2$ 0.9587); indicating the sensor-electrode PA-PPE-APBA-HgbA1c has a high sensitivity and stability.

Figure 8A:
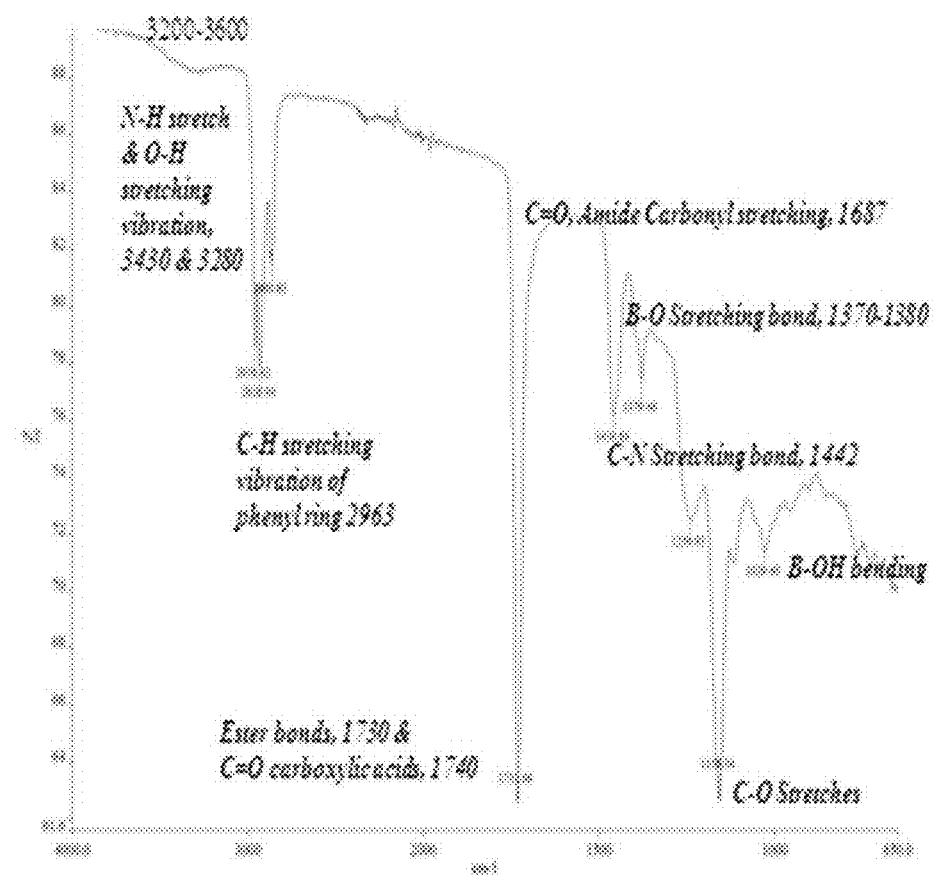
FIGS. 8A-8B. Fourier Transfer InfraRed for PA-PPE-APBA (FIG. 8A) and Fourier Transfer InfraRed for PA-PPE-APBA-HgbA1c (FIG. 8B).

The FT-IR spectrum was compared between APBA and the APBA-HgbA1c, through the PA-PPE-APBA and PA-PPE-APBA-HgbA1c electrodes, to show the differences that occur when the HgbA1c bound APBA and is immobilized. The FT-IR spectrum of APBA (FIG. 8A) exhibits basically two peaks (i) amide I band 1,732 $cm^{-1}$ peak (1,659-1,841 $cm^{-1}$) caused by ester bonds, C=O stretching vibrations in carboxylic acid and carbonyl moieties, 1,740 $cm^{-1}$ for C=O from carboxylic acids and carbonyl moieties; 1452 $cm^{-1}$ for C—N stretching; ester bonds at 1,730 $cm^{-1}$ and the wide band 1,600 $cm^{-1}$ to 1,700 $cm^{-1}$ identified C=O stretching vibrations of peptide linkages in the backbone. (ii) Amide band II 1,456 $cm^{-1}$ peak caused for combinations of N—H in a plane bending and C—N band stretching linkages, at 1,457 $cm^{-1}$ for the peptide groups (1,490 $cm^{-1}$ identified as the combination of N—H in-plane bending and C—N stretching of the peptide groups at 1,442 $cm^{-1}$). A third peak was observed, (iii) Amide band III on 1,239 $cm^{-1}$, correlated with Delfino data's; a fourth peak (iv) B—O stretching vibrations at 1379 $cm^{-1}$ (near 1,370 $cm^{-1}$ broad asymmetric B—O stretching band. Additionally (v) two wide bands in the region 3400 to 3300 $cm^{-1}$ representing the amide A and B bond linkages to B—OH and NH stretching overlapped with O—H stretching vibration were observed, and —$CH_3$ stretching at 3,430 $cm^{-1}$, correlated with previous studies; a sixth peak (vi) characteristic B—O stretches at 1,380 $cm^{-1}$ and 1,350 $cm^{-1}$ and aromatic B—OH bending can be also observed at 1,029 and 860 $cm^{-1}$ after reaction, suggesting the successful amidation reaction of the anchored carboxyl groups with the amine groups of APBA, (a strong band at 1,350 $cm^{-1}$, and weak absorption band at 850 $cm^{-1}$, a seventh peak (vii) C—O stretching vibrations at 1,239 $cm^{-1}$ and 1,158 $cm^{-1}$ (assigned as vCO asym. at 1,238 $cm^{-1}$ and vCO sym. at 1,149 $cm^{-1}$); an eighth peak (viii) C—H stretching vibrations of phenyl ring at 2,958 $cm^{-1}$ incorporated in the band corresponding to C—H stretching 2,950 $cm^{-1}$ for carboxylic acid groups at 2,800 to 3,050 $cm^{-1}$.

Figure 8B:
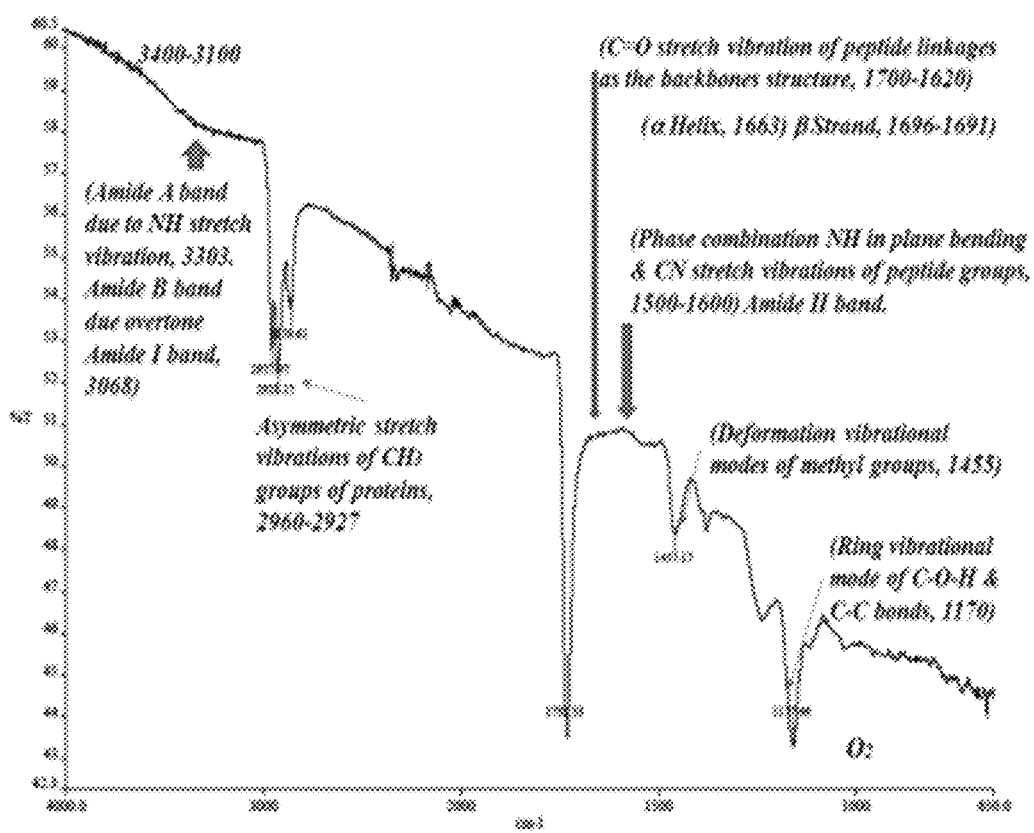
Figure 9:
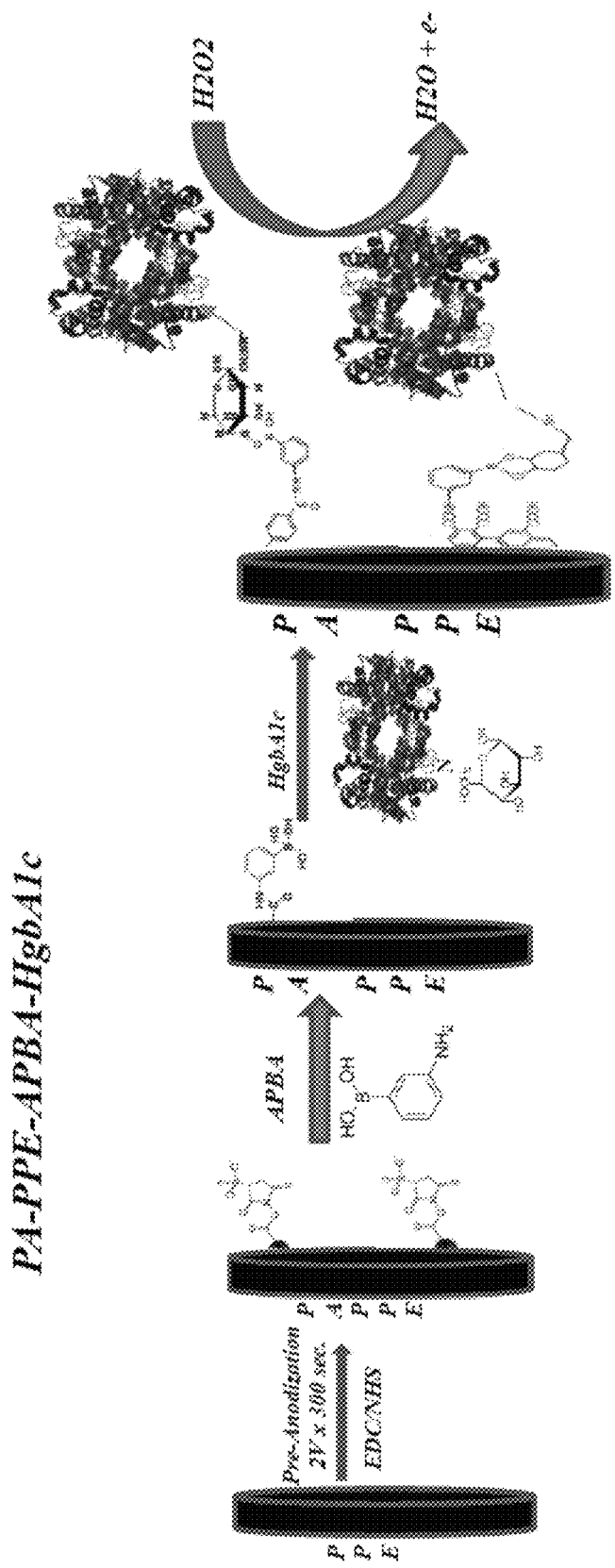
FIG. 9. Design of the PA-PPE-APBA-HgbA1c electrode showing the different steps to immobilization of HgbA1c and the catalytic reaction with $H_2O_2$.
Figure 10:
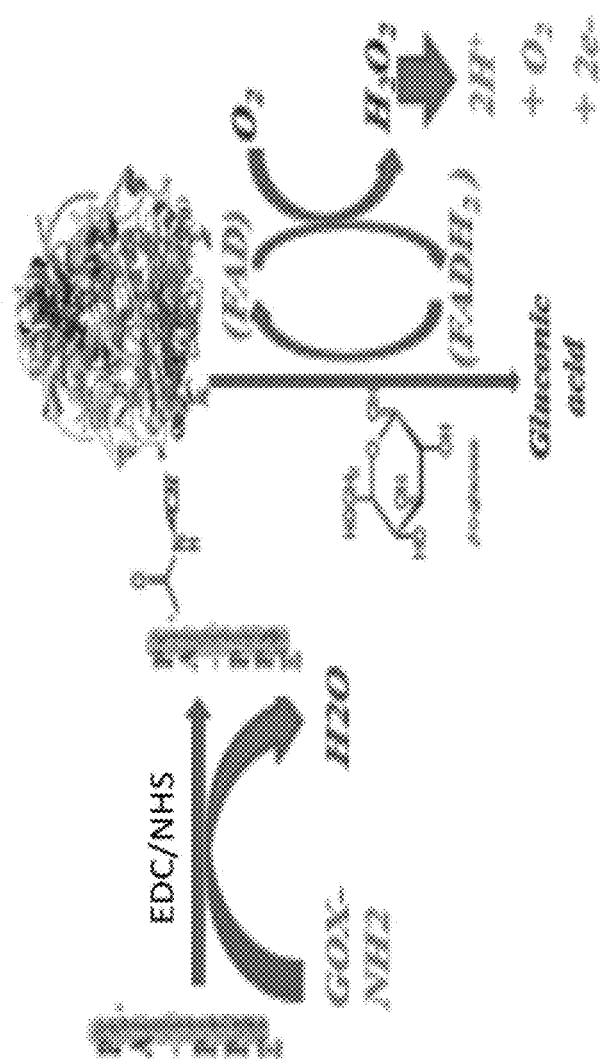
FIG. 10. Schematic representation of fabrication of Modified Electrode: PA-PPE-EDC/NHS-GOX-Glu.

The FT-IR spectrum for Glycated Haemoglobin (HgbA1c) FIG. 8B showed a broad band (i) Amide I band 1,588 to 1,687 $cm^{-1}$ which correspond to C=O stretching of protein amide groups, N—O stretch band for heme group bound NO 1,700 to 1,620 $cm^{-1}$, N—O stretch band for heme-bound near 1,617 $cm^{-1}$ with two discrete N—O stretch bands near 1,617 cm−1 for CI band and 1,632 $cm^{-1}$ for CII band; also will be found absorbance of the amide I band of a protein with α helix near 1,656+/−2 $cm^{-1}$ (~1,654 $cm^{-1}$) and a protein with β sheet structure near between 1,645 and 1,632 cm−1, (~1633 $cm^{-1}$). (ii) A second broad band Amide II band 1,588 $cm^{-1}$ to 1,415 cm−1 for N—H bending vibration strongly coupled to CN stretching vibration of peptide groups of proteins (correlated due to an out-phase combination of N—H in plane bending and C—N stretching vibrations of peptide groups. (iii) A third peak 1,156 $cm^{-1}$ involved in a wide band $O_2$ bound to $Fe^{+2}$ for C—O—H and C—O—C bonds ring vibrational mode of C—O—H and C—O—C bonds at 1,170 $cm^{-1}$. (iv) A fourth wide band with particular variations and absorbance between 1,978 $cm^{-1}$ to 1,825 cm−1 for C—O stretch band in the carbonyl spectrum at the heme bound C—O and cysteine band, also C—O stretch band for heme-bound CO at 1,951 $cm^{-1}$ and bisignate cysteine band at 1,857 $cm^{-1}$. (v) A fifth wide band between 3,400 to 3,050 $cm^{-1}$ for Amide B band and Amide A band due to N—H stretching vibrations, —OH stretching (Gunasekaran et al., *Asian Journal of Chemistry*, 2010, 22(1):51-6; Prasad et al., *RSC Advances*, 2015, 5:11845-49) (3,303 Amide-A band due to N—H stretching vibration and 3,068 Amide-B band due to overtone of Amide I band). Amide I Band (1,693 to 1,632 cm−1) and Amide II band 1,560 to 1,445 cm−1 (Chen and Spiro, *Journal Phys. Chem. A*, 2002, 106:3413-19).

The pre-anodized paper printed electrode transducer to detect HgbA1c (PA-PPE-APBA-HgbA1c) showed high sensitivity (detection limit range 4.54 ng/5 mL), selectivity, stability and feasibility.

Example 2

Direct Electron Transfer of Glucose Oxidase on Pre-Anodized Paper Electrode Modified Through Zero Length Cross-Linker A. Materials and Reagents Glucose Oxidase (GOX), EC 1.1.3.4 from *Aspergillus Niger*, Sigma, b-D-glucose, (1-ethyl-3[dimethylaminopropyl] carbodiimide hydrochloride (EDC) and N-Hydroxysuccinimide (NETS) were purchased from Sigma Aldrich Co. Graphene Oxide (HC-GO, Carbon 79% and Oxygen 20%) was purchased from Graphene Laboratories. A pH 7.4 phosphate buffer solution (PBS) was used in all studies. Water was obtained from a Millipore purification system. Voltammetric measurements were carried out with a CH Instrument (CHI 627) electrochemical workstation with electrodes consists of Paper-carbon electrode (PPE), Graphene Oxide-PPE (GO-PPE), and Preanodized-PPE (PA- PPE). At first, the PPE was fabricated by pattering electrode designs onto a low tack paper, which is subsequently pasted onto a SU8 treated chromatography paper (Dungchai et al., *Analytical Chemistry*, 2009, 81:5821-26; Martinez et al., *Analytical Chemistry*, 2010, 82(1), 3-10; Nie et al., *Lab on a Chip*, 2010, 10:477-83; Lan et al., *Lab on a Chip*, 2013, 13:4103-08; Liu et al., *Electroanalysis*, 2014, 26:1214-23) which was then stencil printed by using conductive carbon and Ag/AgCl ink procured form Conductive Compounds Inc. Houston, to develop a carbon based working electrode (WE), and counter electrode (CE) and silver pseudo reference electrode (RE). The FT-IR spectrum was recorded by using Spectrum 100 FT-IR Spectrometer, Perkin Elmer.

Fabrication of Modified Electrode.

At first, the PPE was pre-anodized by applying a potential at 2.0 V vs. Ag/AgCl for 300 s in pH 7.4 PBS to create carbon and oxygen functionalities, further the immobilization of GOX was carried out through a covalent immobilization fashion (availing EDC/NHS chemistry). The GOX solution was prepared by dissolving 20 mg GOX in 1 mL PBS, and drop coated (5 □L) on to EDC/NHS activated PA-PPE. The electrodes were then dried at room temperature for 2 h, and subsequently washed with PBS to remove unbounded GOX and evaluated for the electrochemical oxidation of glucose through direct electron transfer without utilizing any mediators.

B. Results

Figure 11:
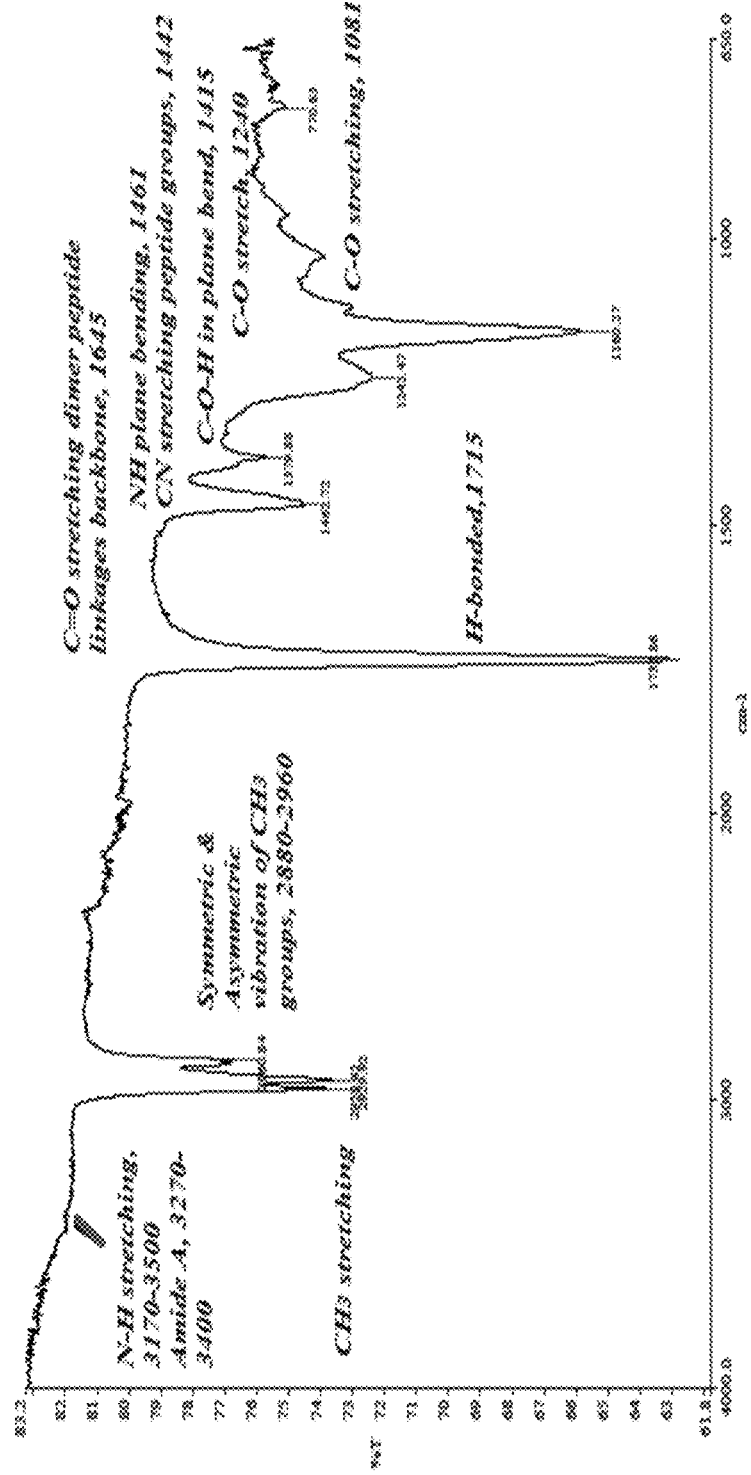
FIG. 11. FT-IR for PA-PPE-GOX.

As can be seen from the FT-IR spectrum of GOX immobilized PA-PPE (FIG. 11), (i) the Amide I band (is an overlapping spectrum of a-helices, b-sheets, turns and random coils, which form the basic structure of the protein) (Zhao et al., *Carbon*, 2010, 48:1508-14) at 1650 cm$^{-1}$ and 1715 cm$^{-1}$ caused by C=O stretching vibrations of peptide linkages in the backbone of the protein GOX; identified C=O stretching vibrations of peptide linkages in the GOX backbone, 1,600 cm$^{-1}$ to 1,700 cm$^{-1}$ (Liang and Zhuobin *Sensors*, 2003, 3:544-54) and 1,650 cm$^{-1}$ to 1,750 cm$^{-1}$, (Hui et al., *Materials Letters*, 2013, 108:88-91); (ii) Amide band II peak at 1,462 cm$^{-1}$ caused for combinations of N—H in a plane bending and C—N stretching linkages for the peptide groups, (1,490 cm$^{-1}$ identified as the combination of N—H in-plane bending and C—N stretching of the peptide groups) (Hui et al., *Materials Letters*, 2013, 108:88-91; Liang and Zhuobin *Sensors*, 2003, 3:544-54; Malasevic et al., *Nanotechnology*, 2008, 19:305604); and (iii) another third small band, amide band III on 1,239 cm$^1$, correlated with Delfino. (Delfino et al., *Materials Science and Engineering C*, 2013, 33:304-10). Additionally, it was found that two wide bands identified in the region 3,400 to 2,900 cm$^{-1}$ representing the amide A and the bond linkages to —CH$_3$ stretching at 3,400 cm$^{-1}$ and 2,958 cm$^{-1}$, respectively, correlated with the Prasad study. (Prasad et al., *RSC Advances*, 2015, 5:11845-49). According to research the presence of Amide I and Amide II in the FT-infrared spectrum of the free enzyme is generally accepted as indicative of the enzymatic activity, and could be used to monitor the GOX characteristics after immobilization.

Figure 12:
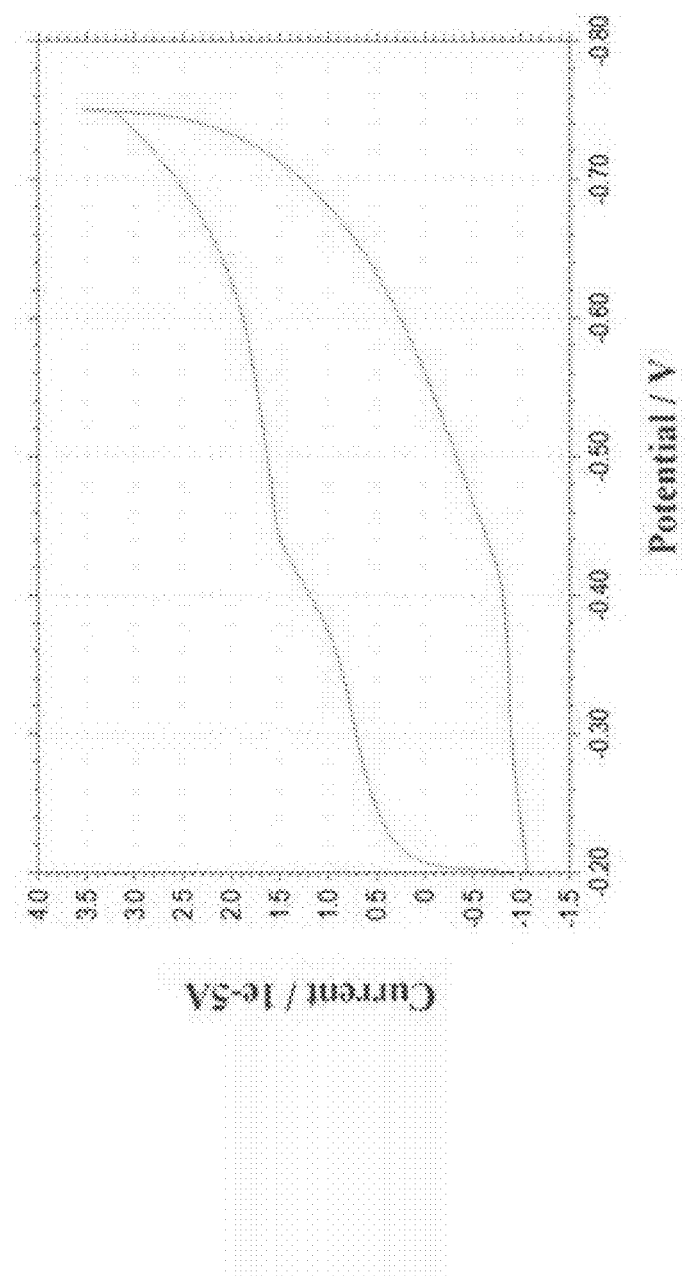
FIG. 12. CV response of PA-PPE immobilized with GOX in 0.1 M PBS at a scan rate of 50 mV/s.

After immobilizing GOX onto PA-PPE, the electrochemical studies were carried out in 0.1 M PBS under N$_2$ (FIG. 12). The Cyclic voltammogram (CV) profile for PA-PPE-GOX exhibited a pair of well-defined and nearly symmetric redox peaks with a formal potential of −0.44 V, which is similar to the previous reports (Yang et al., *Electrochemistry Communications*, 2008, 10:1094-97) and also close to the standard electrode potential of GOX (Kang et al., *Biosensors and Bioelectronics*, 2009, 25:901-05). In addition the CV clearly indicate that the redox peaks are derived from the immobilized GOX, while comparing to the unmodified electrodes without GOX, The electrochemical response of GOX immobilized onto the PA-PPE is attributed to the direct electron transfer of GOX for the conversion of FAD/FADH$_2$ (Yang and Hung, *Electrochemistry Communications*, 2008, 10:1094-97; Cai and Chen. *Analytical Biochemistry*, 2004, 325:285-92; Wang et al., *Analytical Chemistry*, 2002, 74:1993-97). The direct electron transfer reaction of GOX/FAD redox reaction involved two-electron coupled with two-proton transfer, GOX/FAD+2e$^-$+2H$^+$=GOX/FADH$_2$.

Figures 13A, 13B:
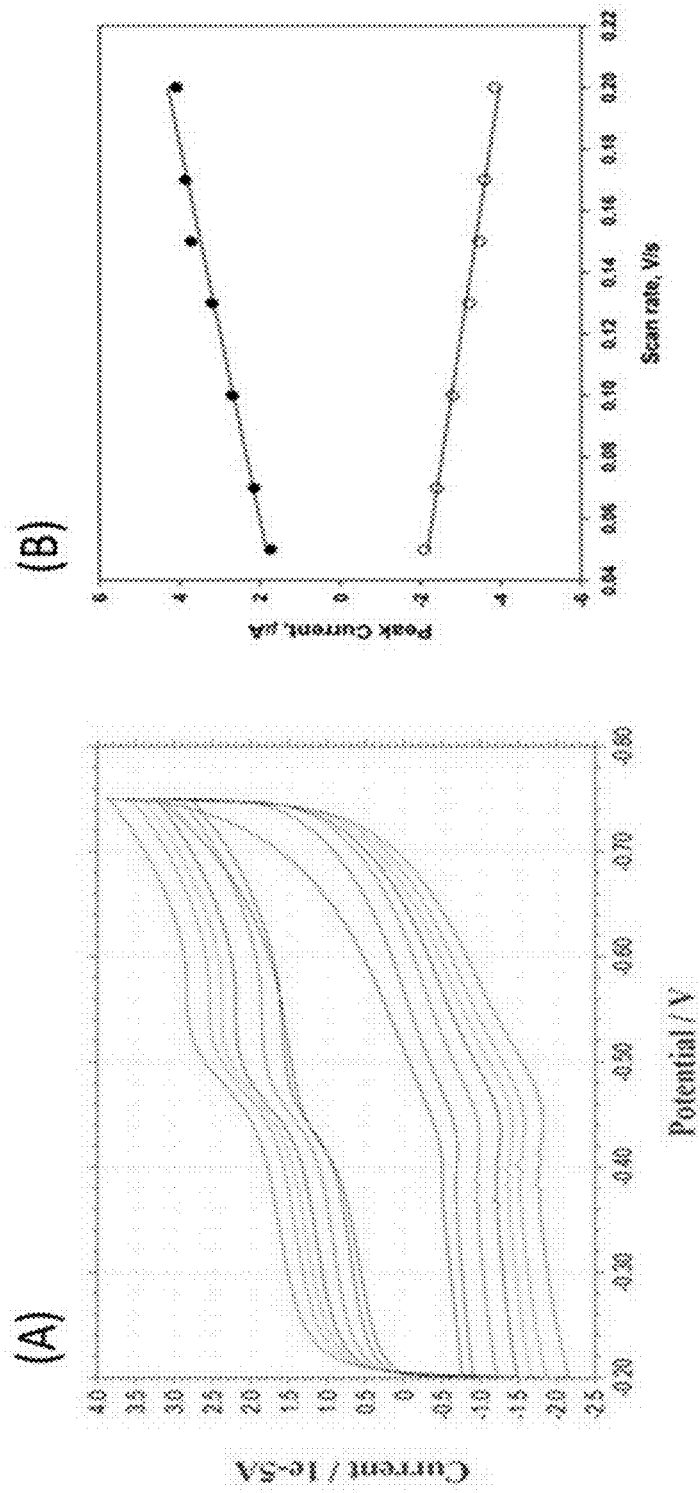
FIGS. 13A-13B.

The scan rate effect on PA-PPE-GOX electrodes is shown in FIG. 13, the CV's at different scan rates ranged from 50 to 200 mV/s (FIG. 13A). The anodic and cathodic peak currents changed appreciable and increased with respect to the change in scan rate and exhibited a good linear relationship for the both anodic and cathodic current and scan rate (FIG. 13B), indicates a surface-controlled redox process. The electron transfer rate constant, $k_s$ for the modified electrode, PA-PPE-GOX was calculated using Laviron equation (Laviron, *J. Electroanal. Chem.*, 1979, 101:19-28).

$$\log k_s = \alpha \log(1-\alpha) + (1-\alpha)\log \alpha - \log(RT/nFv) - \alpha(1-\alpha) nF\Delta Ep/2.3RT$$

The calculated charge transfer coefficient (□) was 0.5617 and with two electrons transfer (n=2), the electron transfer rate constant $k_s$ was calculated to be 3.363 s$^{-1}$, which is higher than the $k_s$ reported for the carbon nanostructured materials (Janegitz et al., *Sensors and Actuators B*, 2011, 158:411-17; Kang et al., *Biosensors and Bioelectronics*, 2009, 25:901-05; Hua et al., *Analyst*, 2012, 137:5716-19; Razmi and Mohammad-Rezaei, *Biosensors and Bioelectronics*, 2013, 41:498-504) and gold nanoparticle incorporated matrices (Wu and Hu, *Bioelectrochemistry*, 2007, 70:335-41; Zhang et al., *Sensors and Actuators B: Chemical*, 2011, 158:23-27). From this it is evident that the oxygen functionalities and edge plane-like sites formed during the pre-anodization process at PPE play an important role in improving the electron transfer communication between the redox centers of GOX and electrode.

Figures 14A, 14B, 14C:
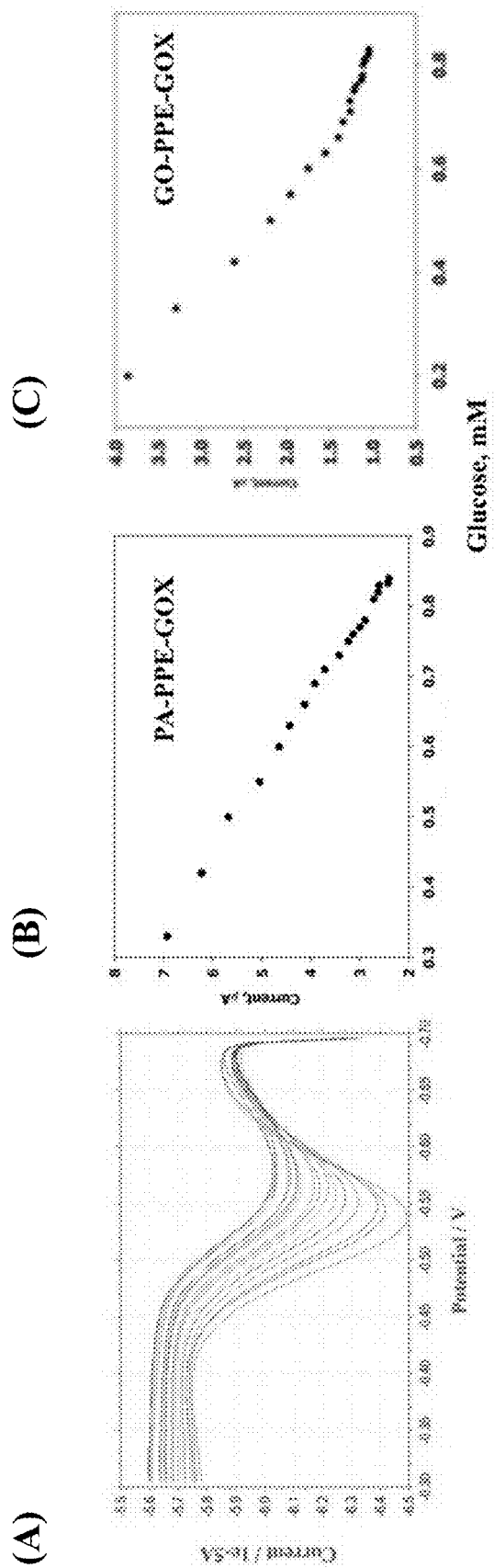
FIGS. 14A-14C. Square wave voltammogram for different concentrations of glucose at PA-PPE-GOX (FIG. 14A) and corresponding calibration curve for PA-PPE-GOX (FIG. 14B) and GO-PPE-GOX (FIG. 14C).

The electrocatalytical activity of the PA-PPE-GOX towards glucose is studied by conducting square wave voltammetry (SWV) experiments with different concentration of glucose ranging from 0.2 mM to 0.84 mM in 0.1 M PBS solution under N$_2$. Successive addition of glucose resulted in a gradual decrease in reduction current (FIG. 14A), and it is linearly proportional to the increased concentration for glucose. This trend could be explained by the fact that addition of glucose triggers the enzyme-catalyzed reaction of GOX and glucose by formation of FADH$_2$ from FAD, at level of the biosensor surface with subsequent decrease of the cathodic peak current (Janegitz et al., *Sensors and Actuators B*, 2011, 158:411-17; Liu et al., *RSC Advances*, 2014, DOI 10.1039/C4RA04975F). This reaction causes a decrease in the amount of oxidized GOX on the PA-PPE electrode and reduces the electrode reduction current. In order to establish the increased sensitivity of the PA-PPE-GOX towards glucose detection the current response was compared to GOX immobilized on graphene oxide through EDC/NHS cross coupling method, GO-PPE-GOX with PA-PPE-GOX. As can be seen from the calibration plots of PA-PPE-GOX (FIG. 14B) and GO-PPE-GOX (FIG. 14C), the pre-anodized electrode exhibited higher current response than GO modified electrodes. The improved electrocatalytical activity at PA-PPE-GOX again point towards the better electron transfer communication between GOX and electrodes at electrochemically activated or pre-anodized electrodes than GO modified electrodes.

Figures 15A, 15B, 15C, 15D:
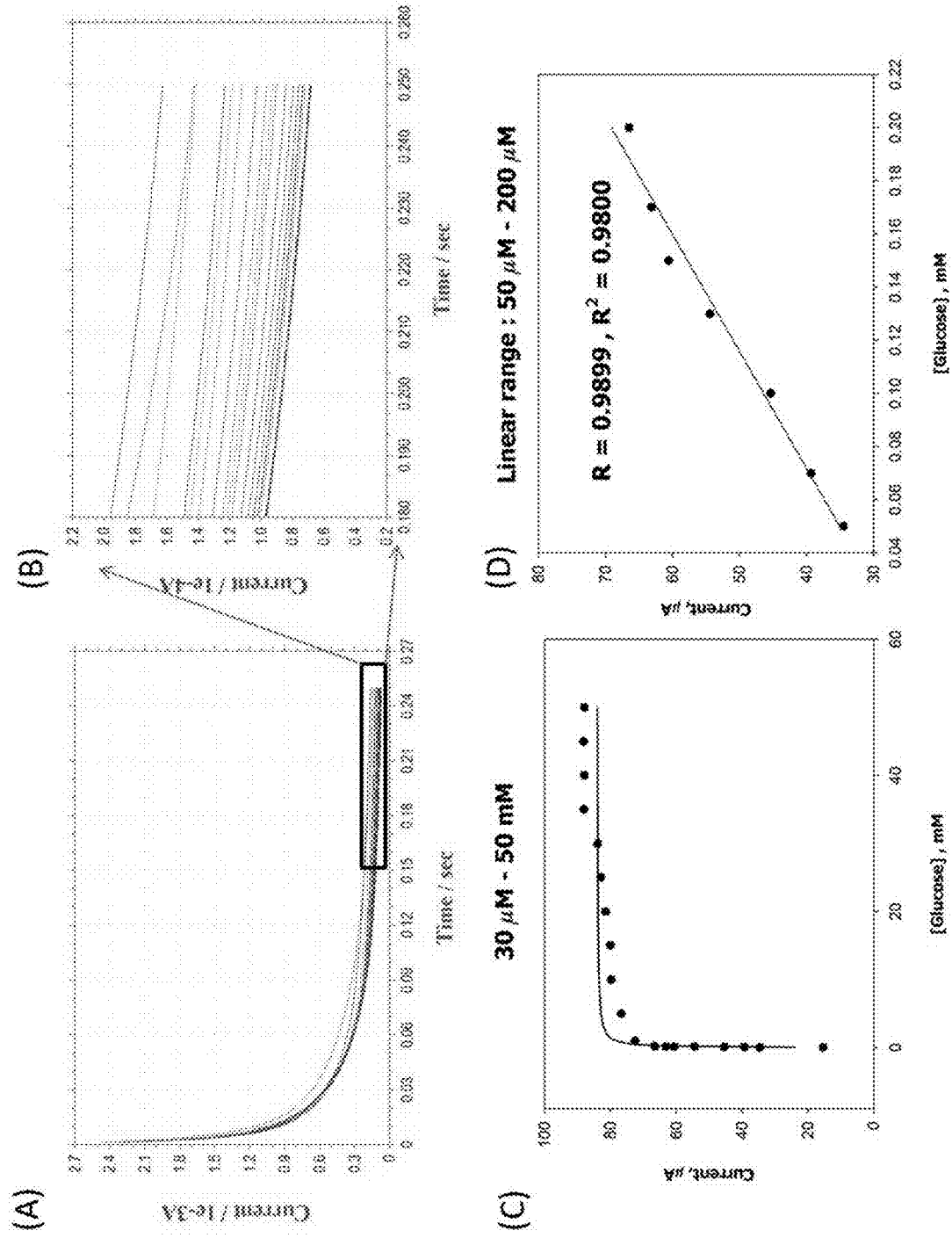
FIGS. 15A-15D. Chronoamperometric response for PA-PPE-GOX towards different concentrations of glucose (30 μM to 50 mM) (FIG. 15A) and (FIG. 15B), and a characteristic response of Michaelis-Menten Kinetics (FIG. 15C), corresponding linearity range of 50 μM to 200 μM (FIG. 15D).

The electrocatalytical activity of PA-PPE-GOX was further characterized by conducting chronoamperometry experiments for the reduction of glucose in 0.1 M PBS (pH 7.4) containing different concentration of glucose, (30 □M to 50 mM). FIGS. 15A and 15B depicts the chronoamperometric (CA) responses of glucose reduction at different concentrations of glucose at −0.55 V. In addition, the negative operating potential for the detection glucose, eliminates the interference from other electroactive species such as, ascorbic acid, uric acid, and dopamine present in the real samples. As the concentration of glucose increases, there is a shift from the linearity between concentration and current (FIG. 15C), exhibiting a typical Michaelis-Menten kinetics (Marcos et al., *Analytica Chimica Acta,* 1993, 283:429-38; Shirale et al., *Int. J. Electrochemistry Sci.,* 2006, 1:62-70). The Lineweaver-Burk plot (Liu et al., *RSC Advances,* 2014, DOI 10.1039/C4RA04975F) a double reciprocal plot, show a linear curve graphic, based in the following equation $1/v = (1/v_{Max}) + \{(Km/v_{Max}).(1/[S])\}$, which corresponds with the linear equation y=b+mx, with a direct correlation between current 1/v (1/mA) and glucose concentration 1/[S] (1/mM) (Shirale et al., *Int. J. Electrochemistry Sci.,* 2006, 1:62-70). The $K_m$ calculated was found to be 0.03 mM, which is lower than GOX immobilized on graphene quantum dot (Razmi and Mohammad-Rezaei. *Biosensors and Bioelectronics,* 2013, 41:498-504), GOX immobilized reduced graphene oxide (Sehat et al., *Int. J. Electrochem. Sci.,* 2014, 10(20145):272-86), poly (p-phenylenediamine)-based nanocomposite,[45] (Baghayeri, *RSC Advances,* 2015, 5:18267-74), and also with the GOX adsorbed pre-anodized screen printed-carbon electrodes (Yang et al., *Electrochemistry Communications,* 2008, 10:1094-97). A lower $K_m$ means the higher enzymatic activity of immobilized GOX at PA-PPE, thus the aforementioned results suggests that the present PA-PPE-GOX have high affinity towards glucose.

The invention claimed is:

1. A glycated hemoglobin sensor comprising a conductive carbon ink printed electrode on a paper support having a functionalized surface coupled to a sugar reactive moiety, wherein the sugar reactive moiety binds glycated hemoglobin and is 3-AminoPhenyl-Boronic Acid (APBA) and wherein the conductive carbon contains surface carbonyl functionalities on edge plane sites.

2. A diagnostic device comprising the sensor of claim 1.

3. A method of detecting glycated hemoglobin comprising (i) contacting a sensor of claim 1 with a sample to form an exposed sensor, and (ii) contacting the exposed sensor with a glycated hemoglobin detection reagent that produces a detectable signal in the presence of hemoglobin.

4. The method of claim 3, wherein the detection reagent is $H_2O_2$.

5. The method of claim 3, wherein the detectable signal is an electric signal.

6. The method of claim 5, wherein the signal is generated by direct electron transfer.

7. The method of claim 3, wherein the sample is blood or a blood fraction.

* * * * *